United States Patent
Goble et al.

[11] Patent Number: 6,056,746
[45] Date of Patent: *May 2, 2000

[54] ELECTROSURGICAL INSTRUMENT

[75] Inventors: Nigel Mark Goble, Nr. Cardiff; Colin Charles Owen Goble, South Glamorgan, both of United Kingdom

[73] Assignee: Gyrus Medical Limited, Cardiff, United Kingdom

[*] Notice: This patent is subject to a terminal disclaimer.

[21] Appl. No.: 09/049,728

[22] Filed: Mar. 27, 1998

Related U.S. Application Data

[63] Continuation-in-part of application No. 08/702,512, filed as application No. PCT/GB96/01473, Jun. 20, 1996.

[30] Foreign Application Priority Data

| Jun. 23, 1995 | [GB] | United Kingdom | 9512888 |
| Jun. 23, 1995 | [GB] | United Kingdom | 9512889 |
| Jan. 9, 1996 | [GB] | United Kingdom | 9600352 |
| Jan. 9, 1996 | [GB] | United Kingdom | 9600355 |

[51] Int. Cl.$^7$ ............................................. A61B 17/39
[52] U.S. Cl. .............................. 606/48; 606/41; 607/105
[58] Field of Search .................... 606/32–34, 41, 606/42, 45–50; 607/100–105; 604/21, 22, 114

[56] References Cited

U.S. PATENT DOCUMENTS

| Re. 33,925 | 5/1992 | Bales et al. . |
| 164,184 | 6/1875 | Kidder . |
| 1,366,756 | 1/1921 | Wappler . |
| 1,735,271 | 11/1929 | Groff . |
| 0 219568 | 12/1985 | European Pat. Off. . |
| 1,814,791 | 7/1931 | Ende . |
| 1,889,609 | 11/1932 | Mutscheller . |
| 1,932,258 | 10/1933 | Wappler . |
| 1,943,543 | 1/1934 | McFadden . |
| 1,952,617 | 3/1934 | Wappler . |
| 1,983,669 | 12/1934 | Kimble . |
| 2,050,904 | 8/1936 | Trice . |
| 2,056,377 | 10/1936 | Wappler . |
| 2,196,171 | 4/1940 | Arnesen . |
| 2,888,928 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |

(List continued on next page.)

FOREIGN PATENT DOCUMENTS

| 0 013605 | 7/1980 | European Pat. Off. . |
| 0 049633 | 4/1982 | European Pat. Off. . |
| 0 067680 | 12/1982 | European Pat. Off. . |
| 0 136855 | 4/1985 | European Pat. Off. . |

(List continued on next page.)

OTHER PUBLICATIONS

Cook, Albert M. & John G. Webster, *Therapeutic Medical Devices Application and Design,* Prentice–Hall Inc., New Jersey, 1982, p. 349.

(List continued on next page.)

*Primary Examiner*—Michael Peffley
*Attorney, Agent, or Firm*—Nixon & Vanderhye P.C.

[57] ABSTRACT

In an electrosurgical instrument for the treatment of tissue in the presence of an electrically conductive fluid medium, a bipolar electrode assembly has an active electrode with an exposed tissue treatment portion, a return electrode having an exposed fluid contact surface, and an insulating member positioned between and electrically insulating the active electrode and the return electrode. The insulating member serves to space apart the exposed active electrode treatment portion and the exposed fluid contact portion of the return electrode. The dimensions and configurations of the exposed portions of the electrodes and of the insulating member are such that, when the electrode assembly is immersed in a conductive fluid medium, the ratio between the longest and shortest conduction path lengths between the active and return electrodes is greater than or equal to 1.25 to 1. The invention also includes a combination of an electrosurgical instrument and a radio frequency generator.

33 Claims, 7 Drawing Sheets

U.S. PATENT DOCUMENTS

| | | |
|---|---|---|
| 3,614,414 | 10/1971 | Gores . |
| 3,648,001 | 3/1972 | Anderson et al. . |
| 3,685,518 | 8/1972 | Beurle et al. . |
| 3,699,967 | 10/1972 | Anderson . |
| 3,707,149 | 12/1972 | Hao et al. . |
| 3,801,766 | 4/1974 | Morrison, Jr. . |
| 3,815,604 | 6/1974 | O'Malley et al. . |
| 3,845,771 | 11/1974 | Vise . |
| 3,847,153 | 11/1974 | Weissman . |
| 3,870,047 | 3/1975 | Gonser . |
| 3,885,569 | 5/1975 | Judson . |
| 3,898,991 | 8/1975 | Ikuno et al. . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,939,839 | 2/1976 | Curtiss . |
| 3,945,375 | 3/1976 | Banko . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison, Jr. . |
| 4,051,855 | 10/1977 | Schneiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,154,240 | 5/1979 | Ikuno et al. . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuler . |
| 4,281,373 | 7/1981 | Mabille . |
| 4,301,802 | 11/1981 | Poler . |
| 4,326,529 | 4/1982 | Doss et al. . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,517,976 | 5/1985 | Murakoshi et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,657,015 | 4/1987 | Irnich . |
| 4,658,819 | 4/1987 | Harris et al. . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,554 | 12/1987 | Ensslin . |
| 4,727,874 | 3/1988 | Bowers et al. . |
| 4,735,201 | 4/1988 | O'Reilly . |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton . |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |
| 5,007,908 | 4/1991 | Rydell . |
| 5,009,656 | 4/1991 | Reimels . |
| 5,013,312 | 5/1991 | Parins et al. . |
| 5,019,076 | 5/1991 | Yamanashi et al. . |
| 5,035,696 | 7/1991 | Rydell . |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. . |
| 5,062,031 | 10/1991 | Flachenecker et al. . |
| 5,071,418 | 12/1991 | Rosenbaum . |
| 5,080,660 | 1/1992 | Buelna . |
| 5,083,565 | 1/1992 | Parins . |
| 5,085,659 | 2/1992 | Rydell . |
| 5,088,997 | 2/1992 | Delahuerga et al. . |
| 5,098,431 | 3/1992 | Rydell . |
| 5,099,840 | 3/1992 | Goble et al. . |
| 5,108,391 | 4/1992 | Flachenecker et al. . |
| 5,108,407 | 4/1992 | Geremia et al. . |

| | | | | | | |
|---|---|---|---|---|---|---|
| 5,117,978 | 6/1992 | Blumenfeld et al. . | | 5,437,662 | 8/1995 | Nardella . |
| 5,122,138 | 6/1992 | Manwaring . | | 5,438,302 | 8/1995 | Goble . |
| 5,133,365 | 7/1992 | Heil, Jr. et al. . | | 5,441,499 | 8/1995 | Fritzsch . |
| 5,158,561 | 10/1992 | Rydell et al. . | | 5,443,470 | 8/1995 | Stern et al. . |
| 5,167,658 | 12/1992 | Ensslin . | | 5,454,809 | 10/1995 | Janssen . |
| 5,167,659 | 12/1992 | Ohtomo et al. . | | 5,462,521 | 10/1995 | Brucker et al. . |
| 5,171,255 | 12/1992 | Rydell . | | 5,472,441 | 12/1995 | Edwards et al. . |
| 5,171,311 | 12/1992 | Rydell et al. . | | 5,472,443 | 12/1995 | Cordis et al. . |
| 5,178,620 | 1/1993 | Eggers et al. . | | 5,480,397 | 1/1996 | Eggers et al. . |
| 5,190,517 | 3/1993 | Zieve et al. . | | 5,480,398 | 1/1996 | Eggers et al. . |
| 5,195,959 | 3/1993 | Smith . | | 5,496,312 | 3/1996 | Klicek . |
| 5,196,007 | 3/1993 | Ellman et al. . | | 5,496,314 | 3/1996 | Eggers . |
| 5,197,963 | 3/1993 | Parins . | | 5,505,728 | 4/1996 | Ellman et al. . |
| 5,201,743 | 4/1993 | Haber et al. . | | 5,505,730 | 4/1996 | Edwards et al. . |
| 5,207,675 | 5/1993 | Canady . | | 5,507,743 | 4/1996 | Edwards et al. . |
| 5,217,457 | 6/1993 | Delahuerga et al. . | | 5,514,129 | 5/1996 | Smith . |
| 5,217,458 | 6/1993 | Parins . | | 5,514,130 | 5/1996 | Baker . |
| 5,217,459 | 6/1993 | Kamerling . | | 5,514,131 | 5/1996 | Edwards et al. . |
| 5,221,281 | 6/1993 | Klicek . | | 5,520,684 | 5/1996 | Imran . |
| 5,244,462 | 9/1993 | Delahuerga et al. . | | 5,520,685 | 5/1996 | Wojciechowicz . |
| 5,249,585 | 10/1993 | Turner et al. . | | 5,522,815 | 6/1996 | Durgin, Jr. et al. . |
| 5,250,047 | 10/1993 | Rydell . | | 5,531,744 | 7/1996 | Nardella et al. . |
| 5,258,006 | 11/1993 | Rydell et al. . | | 5,536,267 | 7/1996 | Edwards et al. . |
| 5,259,395 | 11/1993 | Li . | | 5,540,680 | 7/1996 | Guglielmi et al. . |
| 5,261,906 | 11/1993 | Pennino et al. . | | 5,540,681 | 7/1996 | Strul et al. . |
| 5,267,994 | 12/1993 | Gentelia et al. . | | 5,540,682 | 7/1996 | Gardner et al. . |
| 5,267,997 | 12/1993 | Farin et al. . | | 5,540,683 | 7/1996 | Ichikawa et al. . |
| 5,277,201 | 1/1994 | Stern . | | 5,540,684 | 7/1996 | Hassler, Jr. . |
| 5,277,696 | 1/1994 | Hagen . | | 5,540,685 | 7/1996 | Parins et al. . |
| 5,281,213 | 1/1994 | Milder et al. . | | 5,542,916 | 8/1996 | Hirsch et al. . |
| 5,281,216 | 1/1994 | Klicek . | | 5,542,945 | 8/1996 | Fritzsch . |
| 5,282,799 | 2/1994 | Rydell . | | 5,545,161 | 8/1996 | Imran . |
| 5,282,845 | 2/1994 | Bush et al. . | | 5,545,193 | 8/1996 | Fleischman et al. . |
| 5,290,282 | 3/1994 | Casscells . | | 5,549,605 | 8/1996 | Hahnen . |
| 5,290,283 | 3/1994 | Suda . | | 5,554,172 | 9/1996 | Horner et al. . |
| 5,300,068 | 4/1994 | Rosar et al. . | | 5,555,618 | 9/1996 | Winkler . |
| 5,300,069 | 4/1994 | Hunsberger et al. . | | 5,556,396 | 9/1996 | Cohen et al. . |
| 5,300,070 | 4/1994 | Gentelia et al. . | | 5,556,397 | 9/1996 | Long et al. . |
| 5,304,214 | 4/1994 | DeFord et al. . | | 5,558,671 | 9/1996 | Yates . |
| 5,306,238 | 4/1994 | Fleenor . | | 5,562,720 | 10/1996 | Stern et al. . |
| 5,317,155 | 5/1994 | King . | | 5,569,164 | 10/1996 | Lurz . |
| 5,318,563 | 6/1994 | Malis et al. . | | 5,569,242 | 10/1996 | Lax et al. . |
| 5,320,627 | 6/1994 | Sorenson et al. . | | 5,569,244 | 10/1996 | Hahnen . |
| 5,330,470 | 7/1994 | Hagen . | | 5,569,245 | 10/1996 | Guglielmi et al. . |
| 5,330,471 | 7/1994 | Eggers . | | 5,571,100 | 11/1996 | Goble et al. . |
| 5,334,193 | 8/1994 | Nardella . | | 5,575,789 | 11/1996 | Bell et al. . |
| 5,334,198 | 8/1994 | Hart et al. . | | 5,578,007 | 11/1996 | Imran . |
| 5,336,222 | 8/1994 | Durgin, Jr. et al. . | | 5,582,609 | 12/1996 | Swanson et al. . |
| 5,342,357 | 8/1994 | Nardella . | | 5,582,610 | 12/1996 | Grossi et al. . |
| 5,342,391 | 8/1994 | Foshee et al. . | | 5,584,830 | 12/1996 | Ladd et al. . |
| 5,344,428 | 9/1994 | Griffiths . | | 5,591,141 | 1/1997 | Nettekoven . |
| 5,352,222 | 10/1994 | Rydell . | | 5,599,344 | 2/1997 | Paterson . |
| 5,354,296 | 10/1994 | Turkel . | | 5,599,345 | 2/1997 | Edwards et al. . |
| 5,366,443 | 11/1994 | Eggers et al. . | | 5,599,346 | 2/1997 | Edwards et al. . |
| 5,370,645 | 12/1994 | Klicek et al. . | | 5,599,347 | 2/1997 | Hart et al. . |
| 5,370,675 | 12/1994 | Edwards et al. . | | 5,599,348 | 2/1997 | Gentelia et al. . |
| 5,372,596 | 12/1994 | Klicek et al. . | | 5,599,349 | 2/1997 | D'Amelio . |
| 5,382,247 | 1/1995 | Cimino et al. . | | 5,603,711 | 2/1997 | Parins et al. . |
| 5,383,874 | 1/1995 | Jackson et al. . | | 5,603,712 | 2/1997 | Koranda et al. . |
| 5,383,876 | 1/1995 | Nardella . | | 5,607,422 | 3/1997 | Smeets et al. . |
| 5,383,917 | 1/1995 | Desai et al. . | | 5,609,151 | 3/1997 | Mulier et al. . |
| 5,383,923 | 1/1995 | Webster, Jr. . | | 5,609,573 | 3/1997 | Sandock . |
| 5,395,363 | 3/1995 | Billings et al. . | | 5,611,798 | 3/1997 | Eggers . |
| 5,395,368 | 3/1995 | Ellman et al. . | | 5,620,481 | 4/1997 | Desai et al. . |
| 5,403,311 | 4/1995 | Abele et al. . | | 5,624,439 | 4/1997 | Edwards et al. . |
| 5,419,767 | 5/1995 | Eggers et al. . | | 5,626,560 | 5/1997 | Soring . |
| 5,422,567 | 6/1995 | Matsunaga . | | 5,626,575 | 5/1997 | Crenner . |
| 5,423,808 | 6/1995 | Edwards et al. . | | 5,626,576 | 5/1997 | Janssen . |
| 5,423,809 | 6/1995 | Klicek . | | 5,626,578 | 5/1997 | Tihon . |
| 5,423,810 | 6/1995 | Goble et al. . | | 5,628,745 | 5/1997 | Bek . |
| 5,423,811 | 6/1995 | Imran et al. . | | 5,628,771 | 5/1997 | Mizukawa et al. . |
| 5,431,649 | 7/1995 | Mulier et al. . | | 5,630,426 | 5/1997 | Eggers et al. . |

| | | | | | | |
|---|---|---|---|---|---|---|
| 5,633,578 | 5/1997 | Eggers et al. . | | 2930982 | 2/1981 | Germany . |
| 5,634,924 | 6/1997 | Turkel et al. . | | 3209444 | 10/1982 | Germany . |
| 5,647,869 | 7/1997 | Goble et al. . | | 3215832 | 11/1982 | Germany . |
| 5,672,174 | 9/1997 | Gough et al. . | | 3119735 | 1/1983 | Germany . |
| 5,683,366 | 11/1997 | Eggers et al. . | | 3245570 | 6/1984 | Germany . |
| 5,693,045 | 12/1997 | Eggers . | | 222207 | 5/1985 | Germany . |
| 5,697,281 | 12/1997 | Eggers et al. . | | 3423356 | 1/1986 | Germany . |
| 5,697,536 | 12/1997 | Eggers et al. . | | 3427517 | 1/1986 | Germany . |
| 5,697,882 | 12/1997 | Eggers et al. . | | 3511107 | 10/1986 | Germany . |
| 5,697,909 | 12/1997 | Eggers et al. . | | 3623688 | 1/1987 | Germany . |
| 5,700,262 | 12/1997 | Acosta et al. . | | 3530335 | 3/1987 | Germany . |
| 5,725,524 | 3/1998 | Mulier et al. . | | 3707820 | 9/1987 | Germany . |
| 5,766,153 | 6/1998 | Eggers et al. . | | 3622337 C2 | 1/1988 | Germany . |
| 5,810,764 | 9/1998 | Eggers et al. . | | 3642077 C2 | 6/1988 | Germany . |
| 5,833,689 | 11/1998 | Long . | | 3708801 C2 | 9/1988 | Germany . |
| 5,843,019 | 12/1998 | Eggers et al. . | | 3824913 | 2/1990 | Germany . |
| 5,860,951 | 1/1999 | Eggers et al. . | | 3838840 C2 | 5/1990 | Germany . |
| 5,871,469 | 2/1999 | Eggers et al. . | | 3930451 | 3/1991 | Germany . |
| 5,873,855 | 2/1999 | Eggers et al. . | | 4108269 C2 | 6/1992 | Germany . |
| 5,888,198 | 3/1999 | Eggers et al. . | | 4103972 C2 | 8/1992 | Germany . |
| 5,891,095 | 4/1999 | Eggers et al. . | | 4126608 | 2/1993 | Germany . |
| 5,902,272 | 5/1999 | Eggers et al. . | | 4139029 C2 | 6/1993 | Germany . |

FOREIGN PATENT DOCUMENTS

| | | | | | | |
|---|---|---|---|---|---|---|
| | | | | 4217999 A1 | 12/1993 | Germany . |
| | | | | 4237321 A1 | 5/1994 | Germany . |
| 0 205851 | 12/1986 | European Pat. Off. . | | 4323585 | 1/1995 | Germany . |
| 0 280798 | 9/1988 | European Pat. Off. . | | 4339049 | 5/1995 | Germany . |
| 0 310431 | 4/1989 | European Pat. Off. . | | 4425015 | 1/1996 | Germany . |
| 0 316469 | 5/1989 | European Pat. Off. . | | 19530004 | 3/1996 | Germany . |
| 0 325456 | 7/1989 | European Pat. Off. . | | 4429478 | 3/1996 | Germany . |
| 0 332308 | 9/1989 | European Pat. Off. . | | 19512640 C2 | 10/1996 | Germany . |
| 0 373670 | 6/1990 | European Pat. Off. . | | 19514552 | 10/1996 | Germany . |
| 0 392837 | 10/1990 | European Pat. Off. . | | 19514553 C1 | 10/1996 | Germany . |
| 0 407057 | 1/1991 | European Pat. Off. . | | 19526243 C1 | 1/1997 | Germany . |
| 0 412426 | 2/1991 | European Pat. Off. . | | 19526244 | 1/1997 | Germany . |
| 0 437377 | 7/1991 | European Pat. Off. . | | 19543547 C1 | 1/1997 | Germany . |
| 0 448798 | 10/1991 | European Pat. Off. . | | 19630601 | 2/1997 | Germany . |
| 0 499491 | 8/1992 | European Pat. Off. . | | 19537897 | 3/1997 | Germany . |
| 0 507622 | 10/1992 | European Pat. Off. . | | 19542417 | 5/1997 | Germany . |
| 0 509670 | 10/1992 | European Pat. Off. . | | 19542418 | 5/1997 | Germany . |
| 0 517243 | 12/1992 | European Pat. Off. . | | 19542419 | 5/1997 | Germany . |
| 0 518230 | 12/1992 | European Pat. Off. . | | 19545539 | 6/1997 | Germany . |
| 0530400 | 3/1993 | European Pat. Off. . | | 19545756 | 6/1997 | Germany . |
| 0 536440 | 4/1993 | European Pat. Off. . | | 19650797 | 6/1997 | Germany . |
| 0 558316 | 9/1993 | European Pat. Off. . | | 62-211060 | 9/1987 | Japan . |
| 0 558318 | 9/1993 | European Pat. Off. . | | 644491 | 1/1979 | Russian Federation . |
| 0 647435 | 4/1995 | European Pat. Off. . | | 243478 | 7/1946 | Switzerland . |
| 0 653192 | 5/1995 | European Pat. Off. . | | 1361497 | 7/1974 | United Kingdom . |
| 0 667680 | 8/1995 | European Pat. Off. . | | 2037167 | 7/1980 | United Kingdom . |
| 0 674909 | 10/1995 | European Pat. Off. . | | 1583397 | 1/1981 | United Kingdom . |
| 0 684015 | 11/1995 | European Pat. Off. . | | 2133290 | 7/1984 | United Kingdom . |
| 0 688536 | 12/1995 | European Pat. Off. . | | 2145932 | 4/1985 | United Kingdom . |
| 0 692224 | 1/1996 | European Pat. Off. . | | 2161081 | 1/1986 | United Kingdom . |
| 0 694290 | 1/1996 | European Pat. Off. . | | 2164473 | 3/1986 | United Kingdom . |
| 0 697199 | 2/1996 | European Pat. Off. . | | 2177309 | 1/1987 | United Kingdom . |
| 0 709065 | 5/1996 | European Pat. Off. . | | 2179861 | 3/1987 | United Kingdom . |
| 0 714635 | 6/1996 | European Pat. Off. . | | 2213381 | 8/1989 | United Kingdom . |
| 0 717967 | 6/1996 | European Pat. Off. . | | 2214430 | 9/1989 | United Kingdom . |
| 0 732080 | 9/1996 | European Pat. Off. . | | WO 81/03271 | 11/1981 | WIPO . |
| 0 73345 | 9/1996 | European Pat. Off. . | | WO 82/00084 | 1/1982 | WIPO . |
| 0 737447 | 10/1996 | European Pat. Off. . | | WO 82/02488 | 8/1982 | WIPO . |
| 0 740926 | 11/1996 | European Pat. Off. . | | WO 84/03829 | 10/1984 | WIPO . |
| 0 754437 | 1/1997 | European Pat. Off. . | | WO 88/01851 | 3/1988 | WIPO . |
| 57862 | 9/1953 | France . | | WO 90/03152 | 4/1990 | WIPO . |
| 1215305 | 4/1960 | France . | | WO 93/08756 | 5/1993 | WIPO . |
| 1454773 | 10/1966 | France . | | WO 93/13718 | 7/1993 | WIPO . |
| 2313949 | 1/1977 | France . | | WO 93/13816 | 7/1993 | WIPO . |
| 2443829 | 7/1980 | France . | | WO 93/16650 | 9/1993 | WIPO . |
| 2501034 | 9/1982 | France . | | WO 93/19681 | 10/1993 | WIPO . |
| 651428 | 9/1937 | Germany . | | WO 93/19682 | 10/1993 | WIPO . |
| 1007960 | 5/1957 | Germany . | | WO 93/20747 | 10/1993 | WIPO . |
| 2222820 | 11/1973 | Germany . | | WO 93/20877 | 10/1993 | WIPO . |
| 2457900 | 5/1976 | Germany . | | WO 94/04220 | 3/1994 | WIPO . |

| | | |
|---|---|---|
| WO 94/06510 | 3/1994 | WIPO . |
| WO 94/10921 | 5/1994 | WIPO . |
| WO 94/10924 | 5/1994 | WIPO . |
| WO 94/10925 | 5/1994 | WIPO . |
| WO 94/23659 | 10/1994 | WIPO . |
| WO 94/26228 | 11/1994 | WIPO . |
| WO 94/28809 | 12/1994 | WIPO . |
| WO 95/02369 | 1/1995 | WIPO . |
| WO 95/05781 | 3/1995 | WIPO . |
| WO 95/09576 | 4/1995 | WIPO . |
| WO 95/09577 | 4/1995 | WIPO . |
| WO 95/10320 | 4/1995 | WIPO . |
| WO 95/10321 | 4/1995 | WIPO . |
| WO 95/17855 | 7/1995 | WIPO . |
| WO 95/18575 | 7/1995 | WIPO . |
| WO 95/19733 | 7/1995 | WIPO . |
| WO 95/20360 | 8/1995 | WIPO . |
| WO 95/23558 | 9/1995 | WIPO . |
| WO 95/24160 | 9/1995 | WIPO . |
| WO 95/25472 | 9/1995 | WIPO . |
| WO 95/26686 | 10/1995 | WIPO . |
| WO 95/30377 | 11/1995 | WIPO . |
| WO 95/31144 | 11/1995 | WIPO . |
| WO 96/00036 | 1/1996 | WIPO . |
| WO 96/00039 | 1/1996 | WIPO . |
| WO 96/00040 | 1/1996 | WIPO . |
| WO 96/00042 | 1/1996 | WIPO . |
| WO 96/00043 | 1/1996 | WIPO . |
| WO 96/00528 | 1/1996 | WIPO . |
| WO 96/04859 | 2/1996 | WIPO . |
| WO 96/07360 | 3/1996 | WIPO . |
| WO 96/09010 | 3/1996 | WIPO . |
| WO 96/10367 | 4/1996 | WIPO . |
| WO 96/14020 | 5/1996 | WIPO . |
| WO 96/14021 | 5/1996 | WIPO . |
| WO 96/18349 | 6/1996 | WIPO . |
| WO 96/19152 | 6/1996 | WIPO . |
| WO 96/23448 | 8/1996 | WIPO . |
| WO 96/23449 | 8/1996 | WIPO . |
| WO 96/24296 | 8/1996 | WIPO . |
| WO 96/24301 | 8/1996 | WIPO . |
| WO 96/27337 | 9/1996 | WIPO . |
| WO 96/29946 | 10/1996 | WIPO . |
| WO 96/32897 | 10/1996 | WIPO . |
| WO 96/34567 | 11/1996 | WIPO . |
| WO 96/34569 | 11/1996 | WIPO . |
| WO 96/34570 | 11/1996 | WIPO . |
| WO 96/34571 | 11/1996 | WIPO . |
| WO 96/37146 | 11/1996 | WIPO . |
| WO 96/38094 | 12/1996 | WIPO . |
| WO 96/39085 | 12/1996 | WIPO . |
| WO 96/39086 | 12/1996 | WIPO . |
| WO 96/39088 | 12/1996 | WIPO . |
| WO 96/39089 | 12/1996 | WIPO . |
| WO 96/39966 | 12/1996 | WIPO . |
| WO 96/39967 | 12/1996 | WIPO . |
| WO 97/00646 | 1/1997 | WIPO . |
| WO 97/00647 | 1/1997 | WIPO . |
| WO97/24993 | 7/1997 | WIPO . |
| WO97/24994 | 7/1997 | WIPO . |

OTHER PUBLICATIONS

Pearce, John A., *Electrosurgery*, John Wiley & Sons Inc., New York, 1986, pp. 17, 69–75 and 87.

Wyeth, G.A., *Electrosurgical Unit*, pp. 1180–1202.

Everest Medical Technologies, Inc., "Everest Bipolar Laparoscopic Cholecystectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporations, "The Arthrocare Arthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al. "Use of 5F Bipolar Electrosurgical Probe in Endoscopic Urological Procedures," The Journal of Urology, vol. 143, Feb. 1990, pp. 275–277.

Tucker, Robert et al., "A Bipolar Electrosurgical TURP Loop," Abstract of Paper P14–11, $7^{th}$ World Congress on Endourology and ESWL, Nov. 27–30, Kyoto, Japan, 1989, p. 248.

Ramsay, J.W.A. et al., "A Comparison of Bipolar and Monopolar Diathermy Probes in Experimental Animals," Urological Research, Springer–Verlag 1985, 13:99–102.

German Article w/ Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–6.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–75.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation Bipolar vs. Monopolar in the Treatment of Experimental Canine Gastric Ulcer Bleeding," Gastroenetrology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenetrology, vol. 92, No. 5, May 1987, pp. 1101–1108.

Dennis, M.B. et al., "Evaluation of Electrofulguration in Control of Bleeding of Experimentale Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J., "The Bovie Electrosurgical Current Generator—Some Underlying Principles and Results," Archives of Surgery, vol. 18, 1929, pp. 1863–1873.

McLean, A. J., "Characteristics of Adequate Electrosurgical Current," American Journal of Surgery, vol. XVIII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES, $2^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, $2^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering*, Ed. Jacob Kline, Academic Press, Inc., 1998, pp. 99–113.

Selikwitz, Stuart M. et al., "Electric Current and Voltage Recordings on the Myocardium During Electrosurgical Procedures in Canines," *Reprint from Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol.159, pp. 39–43.

Lu, David Y. et al., "Electrical Thermal Angioplasty: Catheter Design Features, In Vitro Tissue Ablation Studies and In Vivo Experimental Findings," AM J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents—With Illustrative Cases*, CRC Press, New York, 1998, p. 93 (commentary on Honig, William M., "The Mechanism of Cutting in Electrosurgery," IEEE Transactions on Biomedical Engineering, Jan. 1975, pp. 58–65).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthoscopic Electrosurgery System, Model 970 Operator's Manual," Feb. 1996.

ELECTROSURGICAL INSTRUMENT

This application is a continuation-in-part of U.S. application Ser. No. 08/702,512, filed Aug. 26, 1996, filed as PCT/GB96/01473, Jun. 20, 1996.

This invention relates to an electrosurgical instrument for the treatment of tissue in the presence of an electrically conductive fluid medium, and to an electrosurgical system apparatus including such an instrument.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural body opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure direct contact of both electrodes with the tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrode.

The electrical junction between the return electrode and tissue can be supported by wetting of the tissue by a conductive solution such as normal saline. This ensures that the surgical effect is limited to the needle or active electrode, with the electric circuit between the two electrodes being completed by the tissue. One of the obvious limitations with the design is that the needle must be completely buried in the tissue to enable the return electrode to complete the circuit. Another problem is one of the orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v, 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

The applicants have developed a bipolar instrument suitable for underwater electrosurgery using a conductive liquid medium.

The present invention provides an electrosurgical instrument for the treatment of tissue in the presence of an electrically conductive fluid medium, the instrument comprising an instrument shaft and an electrode assembly at a distal end of the shaft, wherein the electrode assembly comprises: a single active electrode having an exposed tissue treatment portion a return electrode having an exposed fluid contact surface, and an insulating member positioned between and electrically insulating the active electrode and the return electrode and serving to space apart the exposed treatment portion of the active electrode and the exposed fluid contact surface of the return electrode, the fluid contact surface of the return electrode being set back in the direction of a treatment axis of the assembly from the active electrode exposed treatment portion, and wherein the dimensions and configuration of the exposed treatment portion, the exposed fluid contact surface and the insulation member are such that, when the electrode assembly is immersed in a conductive fluid medium, the ratio of (i) the length of the shortest conduction path ($P_1$) through the fluid medium between the exposed fluid contact surface and that part of the exposed treatment portion which is furthest from the exposed fluid contact surface, to (ii) the length of the shortest conduction path ($P_2$) through the fluid medium between the exposed fluid contact surface and the exposed treatment portion, is greater than or equal to 1.25 to 1.

The invention also provides a method of treating tissue using a bipolar electrode assembly, the assembly including an active electrode and a return electrode, the active electrode having an exposed treatment portion, and the return electrode having an exposed fluid contact surface spaced and set back from the exposed treatment portion, the method comprising the steps of:

(a) introducing the electrode assembly into a selected operation site:

(b) surrounding the electrode assembly with a conductive fluid so that the conductive fluid defines an electrical path between the active and return electrodes;

(c) applying sufficient radio frequency output power to the electrode assembly to increase the temperature of the conductive fluid adjacent to the active electrode treatment portion without creating a layer of vapour around the treatment portion; and (d) locally applying heat by means of the treatment portion to treat tissue while maintaining the return electrode fluid contact surface out of contact with the tissue.

The invention further provides a method of vaporising tissue using a bipolar electrode assembly, the bipolar electrode assembly including an active electrode and a return electrode, the active electrode having an exposed treatment portion, the method comprising the steps of:

(a) introducing the electrode assembly into a selected operation site;

(b) surrounding the electrode assembly with a conductive fluid;

(c) applying sufficient radio frequency output power to the electrode assembly to vaporise the conductive fluid adjacent to the active electrode treatment portion to create a vapour pocket surrounding the treatment portion; and (d) positioning the treatment portion of the active electrode adjacent to the tissue with the vapour pocket in contact with the tissue while maintaining the return electrode out of contact with the tissue.

Still further, the invention provides a method of haemostatically treating tissue using a bipolar electrode assembly, the bipolar electrode assembly including an active electrode and a return electrode, the active electrode having an exposed treatment portion, the method comprising the steps of:

(a) introducing the electrode assembly into a selected operation site, (b) surrounding the electrode assembly with a conductive fluid;

(c) applying maximum radio frequency output power to the electrode assembly to heat the conductive fluid adjacent to the active electrode treatment portion without creating a layer of vapour around the treatment portion;

(d) positioning the treatment portion of the active electrode adjacent to the tissue with the heated conductive fluid in contact with the tissue while maintaining the return electrode out of contact with the tissue.

Still further, the invention provides a method of vaporising and haemostatically treating tissue using a bipolar electrode assembly, the bipolar electrode assembly including an active electrode and a return electrode, the active electrode having an exposed treatment portion, the method comprising the steps of:

(a) introducing the electrode assembly into a selected operation site;

(b) surrounding the electrode assembly with a conductive fluid;

(c) alternating the application of sufficient radio frequency output power to the electrode assembly to (i) vaporise the conductive fluid adjacent to the active electrode treatment portion to create a vapour pocket surrounding the treatment portion, and (ii) to increase the temperature of the conductive fluid adjacent to the active electrode treatment portion without creating a layer of vapour around the treatment-portion; and (d) positioning the treatment portion of the active electrode adjacent to the tissue while maintaining the return electrode out of contact with the tissue.

Another aspect of the invention is as defined in claim 11, which relates to an electrosurgical system including an instrument and a generator. Some of the preferred features of the different aspects of the invention are set out in the dependent claims.

The electrode structure of this instrument, in combination with an electrically-conductive fluid medium largely avoids the problems experienced with monopolar or bipolar electrosurgery. In particular input power levels are much lower than those generally necessary with a monopolar arrangement (typically 100 watts). Moreover, because of the relatively large spacing between its electrodes, an improved depth of effect is obtained compared with conventional bipolar arrangements.

The invention will now be described by way of example with reference to the drawings in which.

Figure 1:
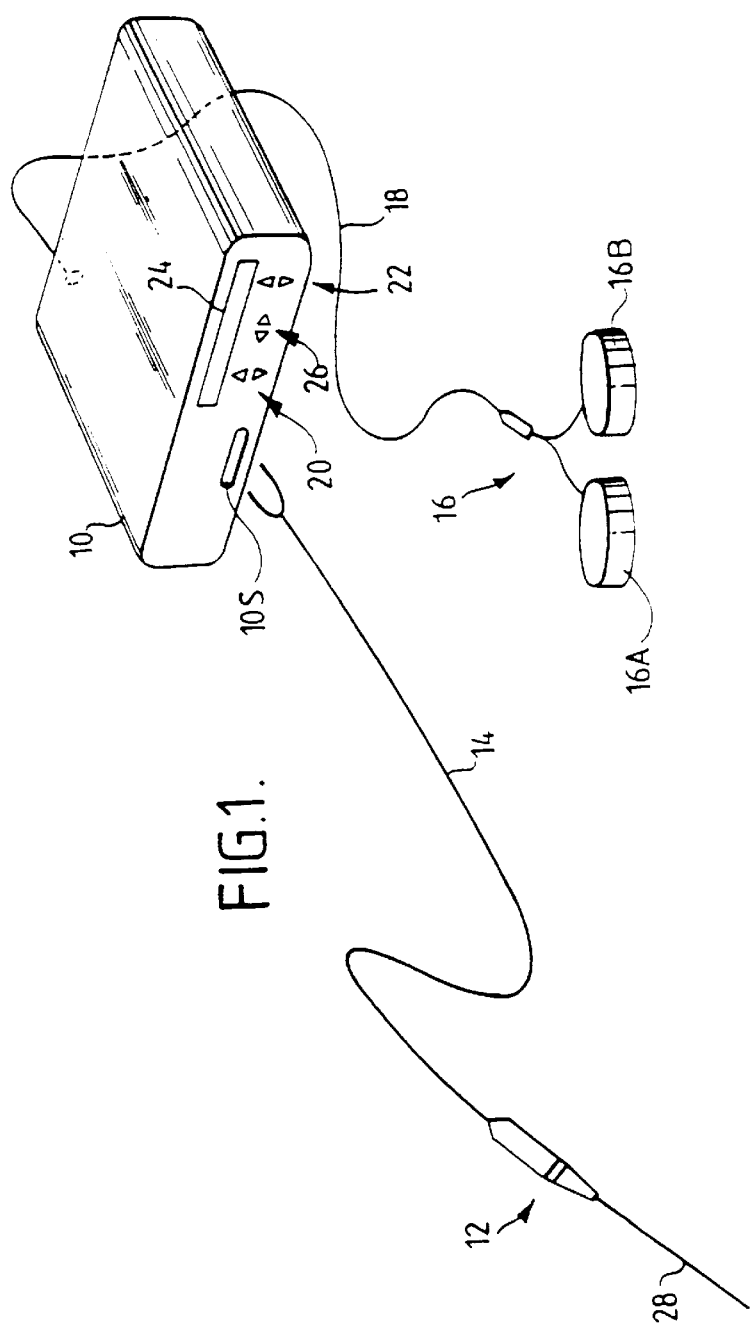
FIG. 1 is a diagram showing an electrosurgical system in accordance with the invention.

Referring to the drawings, FIG. 1 shows electrosurgical apparatus including an electrosurgical generator 10 having an output socket 10S providing a radio frequency (RF) output for a bipolar instrument, in the form of a handpiece 12 and a detachable electrode unit 28, via a connection cord 14. Activation of the generator 10 may be performed from the handpiece 12 via a control connection in the cord 14, or by means of a footswitch unit 16, as shown, connected separately to the rear of the generator 10 by a footswitch connection cord 18. In the illustrated embodiment, the footswitch unit 16 has two footswitches 16A and 16B for selecting a desiccation and coagulation mode and a vaporisation mode of the generator 10 respectively. Coagulation is the process of denaturing of tissue of tissue protein so that it coagulates (or sticks together), and typically occurs at 70° C. to 100° C. Desiccation is the process of removing water from tissue by boiling, and occurs at temperatures of at least 100° C. Because these two modes are contiguous, and require similar operating parameters, they will be referred to as a desiccation mode throughout the specification. The generator front panel has push buttons 20 and 22 for respectively setting desiccation and vaporisation power levels, which are indicated in a display 24. Push buttons 26 are provided as means for selection of different vaporisation modes.

The instrument need not include a handpiece, but may simply include a connector for mounting to another device such as a resectoscope. In FIG. 1 the instrument has an electrode unit 28 which is shown mounted to the handpiece 12.

The electrode unit 28 may take a number of different forms, some of which are described below.

Figure 2:
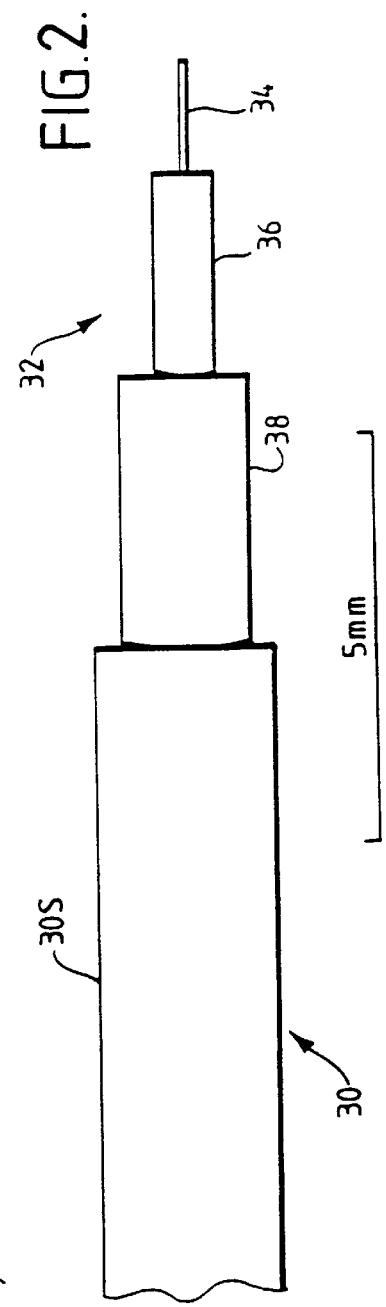
FIG. 2 is a side view of a portion of an electrosurgical instrument forming part of the system of FIG. 1.

In a basic configuration, shown in FIG. 2, an electrode unit for detachable fastening to an instrument handpiece comprises a shaft 30 which may be a conductive tube covered with an insulating sheath 30S, with an electrode assembly 32 at a distal end of the shaft 30. At the other end of the shaft (not shown) means are provided for connecting the unit to a handpiece both mechanically and electrically.

The electrode assembly 32 comprises a central active electrode 34 which is exposed at the extreme distal end of the unit to form a treatment portion of the electrode. Preferably the active electrode is a metallic wire which extends as a central conductor through the whole of the shaft 30 to a contact at the proximal end (not shown in the drawing).

Surrounding the electrode 34 and the inner conductor is an insulating sleeve 36 the distal end of which is exposed proximally of the exposed treatment portion of the electrode 34. Typically, this sleeve is made of a ceramic material to resist damage from arcing. Surrounding the sleeve 36 is the return electrode 38 in the form of a metallic tube which is electrically (and optionally also mechanically) integral with the metallic tubular body of the shaft 30. This return electrode terminates at a point short of the end of the sleeve 36 so that it is set back from the exposed treatment portion of the active electrode 34 and is both radially and axially spaced from the latter. It will be appreciated that, principally due to the much larger diameter of the return electrode in comparison to that of the active electrode, the return electrode provides an exposed fluid contact surface which has a surface area very much greater than that of the exposed active electrode treatment portion. The insulating sheath 30S terminates at a location proximally spaced from the distal end of the return electrode 38 in order to provide the required surface area for the return electrode fluid contact surface. At the distal end of the electrode unit, the diameter of the return conductor is typically in the region of from 1 mm to 5 mm. The longitudinal extent of the exposed part fluid contact surface the return electrode 38 is typically between 1 mm and 5 mm with the longitudinal spacing from the return electrode 38 to the exposed active electrode treatment portion between 1 mm and 5 mm. Further aspects of the configuration and dimensioning of electrode assemblies are set out in more detail below.

In effect, the electrode structure shown in FIG. 2 is bipolar, with only one of the electrodes (34) actually extending to the distal end of the unit. This means that, in normal use when the electrode assembly is immersed in a conductive fluid medium, the return electrode 38 remains spaced from the tissue being treated and a current path exists between the two electrodes via the conductive fluid medium which is in contact with the return electrode, and possibly also via the tissue.

The axial spacing of the electrodes permits a very fine electrode structure in terms of diameter since the insulation path is considerably longer than a bipolar electrode having merely radial spacing between exposed electrode surfaces. This allows higher powers to be used than with conventional electrode structures without causing unwanted arcing, or in the case of electrosurgical cutting or vaporisation treatment, without causing electrode unit damage due to excessive arcing at high temperatures.

The particular staggered arrangement shown affords the surgeon a view of the tissue contact electrode tip, and permits a large range of applied angles with respect to the tissue surface, which is particularly important in the confined spaces typical of endoscopic surgery.

Figure 3:
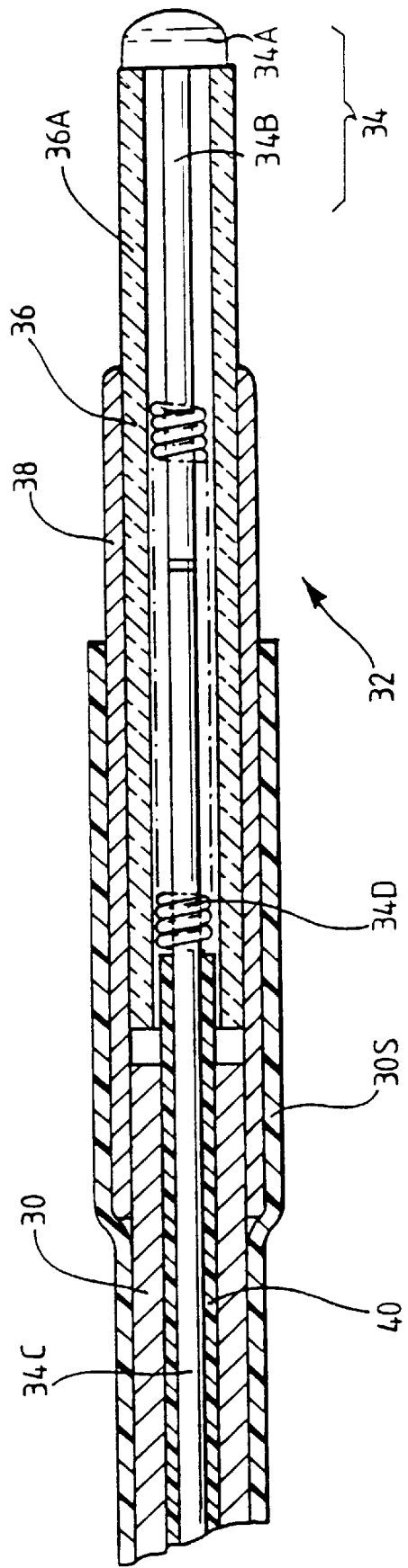
FIG. 3 is a cross-section of part of an alternative electrosurgical instrument in accordance with the invention, the instrument being sectioned along a longitudinal axis.

Referring to FIG. 3, an alternative electrode unit for detachable fastening to the electrosurgical instrument handpiece 12 shown in FIG. 1 comprises a shaft 30, which is constituted by a semi-flexible tube made of stainless steel or phynox electroplated in copper or gold, with an electrode assembly 32 at a distal end thereof. At the other end (not shown) of the shaft 30, means are provided for connecting the electrode unit to the handpiece both mechanically and electrically.

The electrode assembly 32 includes a central, active or tissue contact electrode 34 which is made of platinum, platinum/iridium or platinum/tungsten, and is constituted by a generally hemispherical exposed tip 34A and an integral central conductor 34B. The conductor 34B is electrically connected to a central copper conductor 34C by fastening a thin stainless steel spring 34D over the adjacent end portions of the conductors 34B and 34C, thereby providing an electrical connection between the handpiece of the instrument and the exposed tip 34A. A ceramic insulation sleeve 36 surrounds the conductor 34B, the spring 34D and the adjacent end portion of the copper conductor 34C. The sleeve 36 has an exposed portion 36A which surrounds the distal end portion of the conductor 34B. A return electrode 38, which forms a distal end portion of the shaft 30 providing a cylindrical fluid contact surface, closely surrounds the sleeve 36 and extends over the copper conductor 34C spaced from the latter by an insulation sleeve 40. An outer insulating heat shrink or polyimide coating 30S surrounds the shaft 30 and proximal portion of the return electrode 38.

Figure 4:
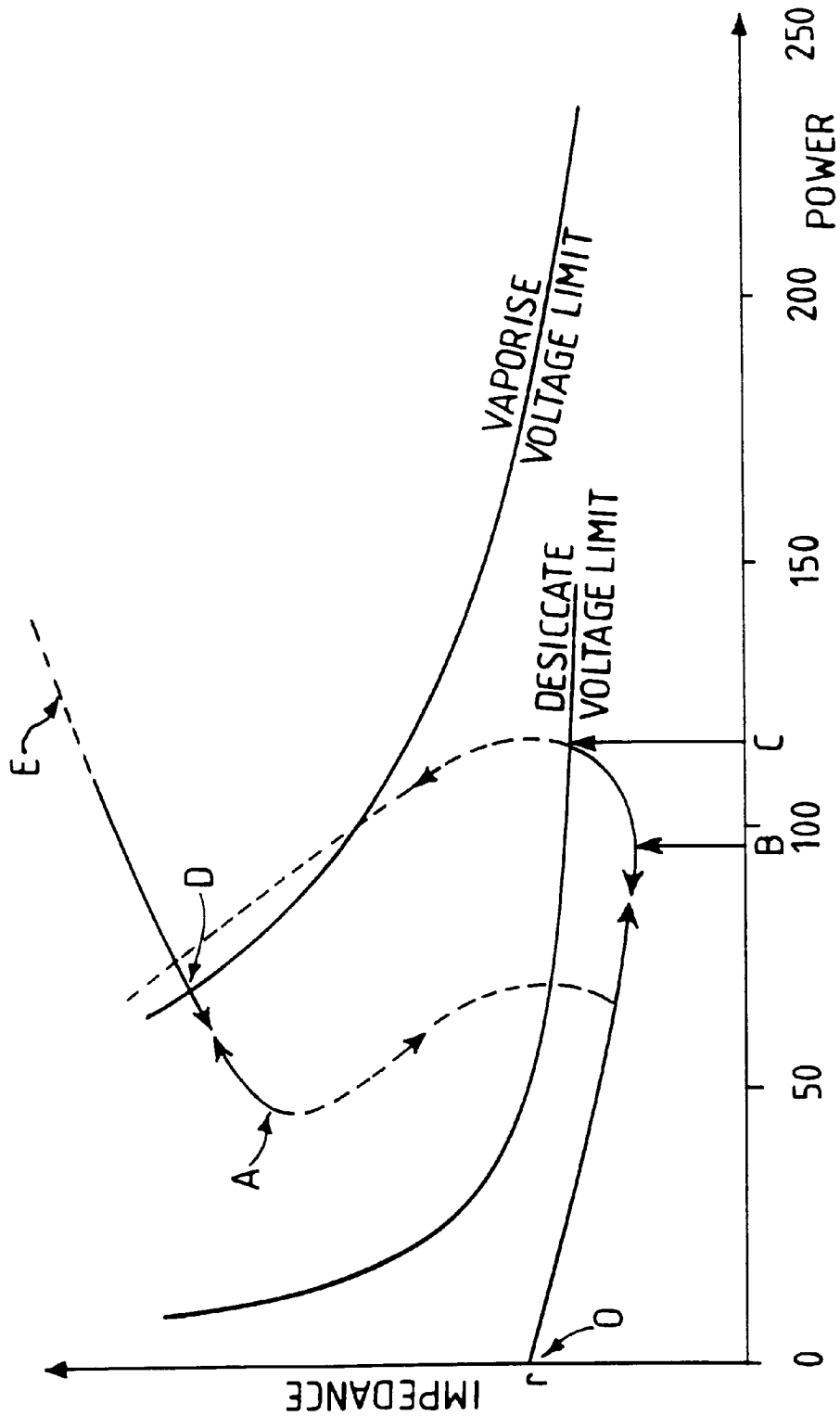
FIG. 4 is a graph illustrating the hysteresis of the electrical load impedance and dissipated radio frequency power which occurs between use of an instrument in accordance with the invention in desiccating and vaporising modes.

When used in combination with an electrosurgical generator as shown in FIG. 1, the electrode unit of FIG. 3 can be employed in a conductive fluid medium for tissue removal by vaporisation, for sculpturing and contouring menisci during arthroscopic surgery, or for desiccation, depending on the manner in which the generator is controlled. FIG. 4 illustrates how the generator can be controlled to take advantage of the hysteresis which exists between the desiccation and the vaporising modes of the electrode unit. Thus, assuming the electrode assembly 32 of the unit is immersed in a conductive medium such as saline, there is an initial load impedance "r" at point "O", the magnitude of which is defined by the geometry of the electrode assembly and the electrical conductivity of the fluid medium. The value of "r" changes when the active electrode 34 contacts tissue, the higher the value of "r" the greater is the propensity of the electrode assembly 32 to enter the vaporisation mode. When RF power is applied to the electrode assembly 32 the fluid medium heats up. Assuming the fluid medium is normal saline (0.9% w/v), the temperature coefficient of conductivity of the fluid medium is positive, so that the corresponding impedance coefficient is negative. Thus, as power is applied, the impedance initially falls and continues to fall with increasing power dissipation to point "B", at which point the saline in intimate contact with the electrode assembly 32 reaches its boiling point. Small vapour bubbles form on the surface of the active tip 34A and the impedance then starts to rise. After point "B", as power dissipation is increased further, the positive power coefficient of impedance is dominant, so that small increases in power now bring about large increases in impedance.

As a vapour pocket forms from the vapour bubbles, there is an increase in the power density at the residual electrode/saline interface. There is, however, an exposed area of the active electrode tip 34A not covered by vapour bubbles, and this further stresses the interface, producing more vapour bubbles and thus even higher power density. This is a run-away condition, with an equilibrium point only occurring once the electrode is completely enveloped in vapour. The only means of preventing the run-away condition is to limit applied voltage, thereby preventing power dissipation into higher impedance loads. For given set of variables, there is a power threshold before this new equilibrium can be reached (point "C").

The region of the graph between the points "B" and "C", therefore, represents the upper limit of the desiccation mode. The transition from point "C" to the vaporise equilibrium state will follow the power impedance curve for the RF stage of the generator (shown as a dotted line in FIG. 4). Once in the vaporisation equilibrium state, the impedance rapidly increases to around 1000 ohms, with the absolute value depending on the system variables. The vapour pocket is then sustained by discharges across the vapour pocket between the active electrode tip 34A and the vapour/saline interface. The majority of power dissipation occurs within this pocket, with consequent heating of the tip 34A. The amount of energy dissipation, and the size of the pocket, depends on the output voltage. If this is too low, the pocket will not be sustained, and if it is too high the electrode assembly 32 will be destroyed. It should be noted that, if power were delivered at the same level as point "C", the resulting voltages would cause electrode destruction. The normal operating point for an electrode used for vaporisation is illustrated by point "D". This point is defined uniquely by the combination of the impedance power characteristic for the electrode in conjunction with the vaporise voltage limit. The dotted line E indicates the power level above which electrode destruction is inevitable. As the power is reduced, the impedance falls until, at point "A", the vapour pocket collapses and the electrode assembly 32 reverts to the desiccation mode. At this point, power dissipation within the vapour pocket is insufficient to sustain it, so that direct contact between the active electrode tip 34A and the saline is re-established, and the impedance falls dramatically. The power density at the tip 34A also falls, so that the temperature of the saline falls below boiling point. The electrode assembly 32 is then in a stable desiccation mode.

Generator power control to achieve the required desiccation, tissue cutting and vaporisation functions is carried out by sensing the peak RF voltage appearing across the output connections of the generator and by rapidly reducing the delivered output power whenever a preselected peak voltage threshold is reached. In a desiccation mode at least, this power reduction is significantly more than that required merely to bring the peak output voltage below the threshold. Preferably the power reduction is at least 50% to take advantage of the hysteresis characteristic descibed above with reference to FIG. 4.

Figure 5:
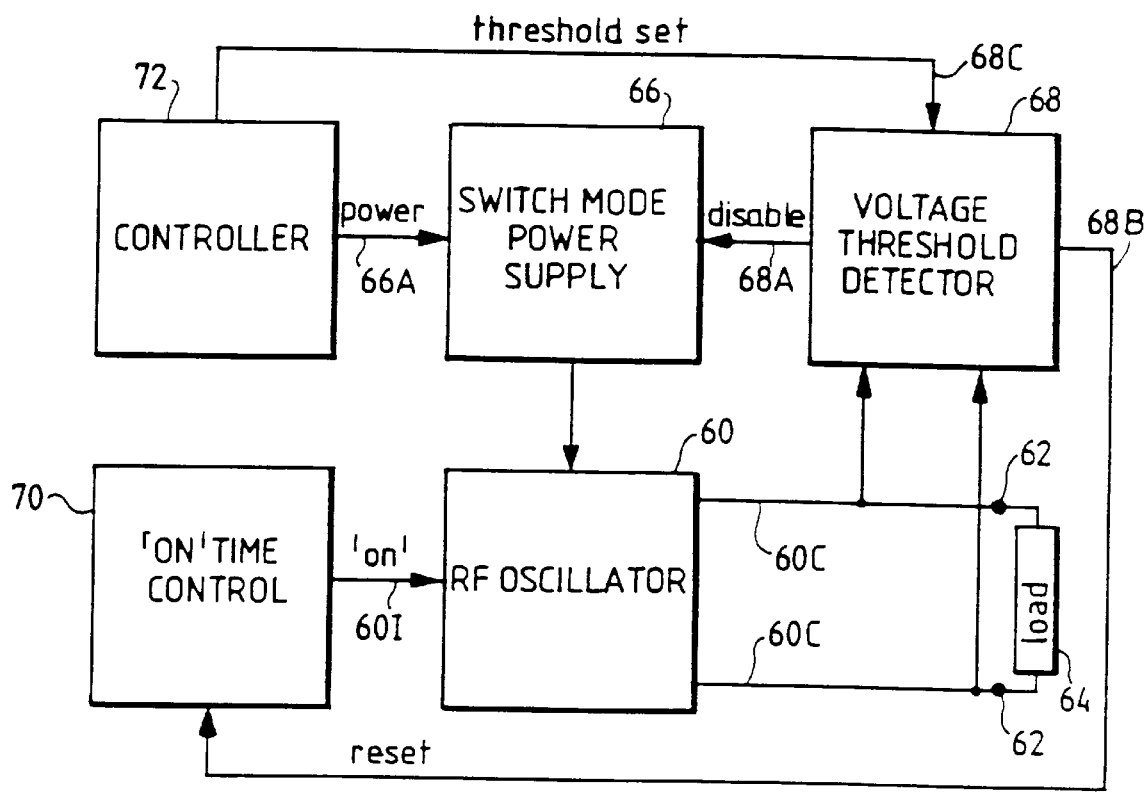
FIG. 5 is a block diagram of the generator of the electrosurgical system shown in FIG. 1.

Referring to FIG. 5, the generator comprises a radio frequency (RF) power oscillator 60 having a pair of output connections 60C for coupling via output terminals 62 to the load impedance 64 represented by the electrode assembly when in use. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output connections 60C is a voltage threshold detector 68 having a first output 68A coupled to the switched mode power supply 66 and a second output 68B coupled to an "on" time control circuit 70. A microprocessor controller 72 coupled to the operator controls and display (shown in FIG. 1), is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a handpiece or footswitch (see FIG. 1). A constant output voltage threshold is set independently of the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required, the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each oscillation cycle. The power delivered to the load 64 depends partly on the supply voltage applied to the RF oscillator 60 from the switched mode power supply 66 and partly on the load impedance 64. If the supply voltage is sufficiently high, the temperature of the liquid medium surrounding the electrodes of the electrosurgical instrument (or within a gaseous medium, the temperature of liquids contained within the tissue) may rise to such an extent that the liquid medium vaporises, leading to a rapid increase in load impedance and a consequent rapid increase in the applied output voltage across terminals 62. This is an undesirable state of affairs if a desiccation output is required. For this reason, the voltage threshold for a desiccation output is set to cause trigger signals to be sent to the "on" time control circuit 70 and to the switched mode power supply 66 when the threshold is reached. The "on" time control circuit 70 has the effect of virtually instantaneously reducing the "on" time of the RF oscillator switching device. Simultaneously, the switched mode power supply is disabled so that the voltage supplied to oscillator 60 begins to fall.

The output voltage of the generator is important to the mode of operation. In fact, the output modes are defined purely by output voltage, specifically the peak output voltage. The absolute measure of output voltage is only necessary for multiple term control. However, a simple single term control (i.e. using one control variable) can be used in this generator in order to confine the output voltage to predetermined limit voltages. Thus, the voltage threshold detector 68 shown in FIG. 5 compares the RF peak output voltage with a preset DC threshold level, and has a sufficiently fast response time to produce a reset pulse for the "on" time control circuit 70 within one RF half cycle.

Maximum absorbed power by the saline/tissue coincides with the electrode condition existing immediately before formation of vapour bubbles, since this coincides with maximum power dissipation and the greatest wetted electrode area. It is therefore desirable that the electrode remains in its wetted state for the maximum desiccation power. Use of voltage limit detection brings about a power reduction which allows the vapour bubbles to collapse which in turn increases the ability of the active electrode to absorb power. It is for this reason, that the generator includes a control loop having a large overshoot, in that the feedback stimulus of the peak voltage reaching the predefined threshold causes a large instantaneous reduction in power by causing a reduction in peak output voltage to a level significantly below the peak output voltage level set by the threshold detector 68. This control overshoot ensures a return to the required wetted state.

Further details of the generator and its operation are described in European Patent Application No. 0754437A.

In the light of the above, it will be apparent that the electrode unit of FIG. 3 can be used for desiccation by operating the unit in the region of the graph between the point "0" and a point in the region between the points "B" and "C". In this case, the electrode assembly 32 is introduced into a selected operation site with the active tip 34A adjacent to the tissue to be treated, and with the tissue and the active tip and the return electrode immersed in the saline. The generator is then activated (and cyclically controlled as described above) to supply sufficient power to the electrode assembly 32 to maintain the saline adjacent to the active tip 34A at, or just below, its boiling point without creating a vapour pocket surrounding the active tip. The electrode assembly is manipulated to cause heating and desiccation of the tissue in a required region adjacent to the active tip 34A. The electrode unit can be used for vaporization in the region of the graph between the point "D" and the dotted line F which constitutes the level below which vaporisation is no longer stable. The upper part of this curve is used for tissue removal by vaporisation. In this mode, a light application of the instrument to the tissue to be treated enables sculpturing and contouring to be carried out.

Figure 6:
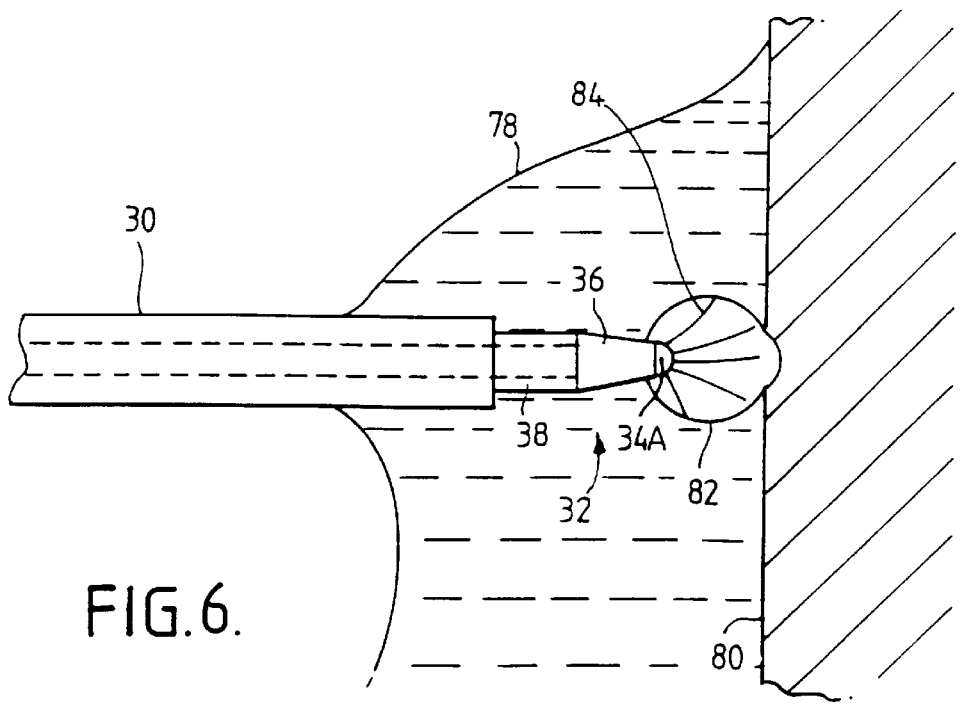
FIG. 6 is a diagrammatic side view of the instrument of FIG. 3 showing the use of the instrument for tissue removal by vaporisation.

FIG. 6 illustrates the use of the electrode unit of FIG. 3 for tissue removal by vaporisation, the electrode unit being immersed in conductive fluid 78. Thus, the electrode unit creates a sufficiently high energy density at the active tip 34A to vaporise tissue 80, and to create a vapour pocket 82 surrounding the active tip. The formation of the vapour pocket 82 creates about a 10-fold increase in contact impedance, with a consequent increase in output voltage. Arcs 84 are created in the vapour pocket 82 to complete the circuit to the return electrode 38. Tissue 80 which contacts the vapour pocket 82 will represent a path of least electrical resistance to complete the circuit. The closer the tissue 80 comes to the active tip 34A, the more energy is concentrated to the tissue, to the extent that the cells explode as they are struck by the arcs 84, because the return path through the conductive fluid (saline in this case) is blocked by the high impedance barrier of the vapour pocket 82. The saline solution also acts to dissolve or disperse the solid products of vaporisation.

In use, the electrode assembly 32 is introduced into a selected operation site with the active electrode tip 34A adjacent the tissue to be vaporised, and with the tissue, the active tip and the return electrode 38 immersed in the saline 78. The RF generator is activated to supply sufficient power (as described above with reference to FIG. 4) to the electrode assembly 32 to vaporise the saline and to maintain a vapour pocket surrounding the tissue contact electrode. When the electrode unit is used for sculpturing or contouring menisci during arthroscopic surgery, the electrode assembly 32 is applied with light pressure at the selected operation site, and is manipulated so that the part-spherical surface of the active tip 34A moves across the surface to be treated, smoothing away tissue, and in particular menisci, with a sculpturing or contouring action.

Figure 7:
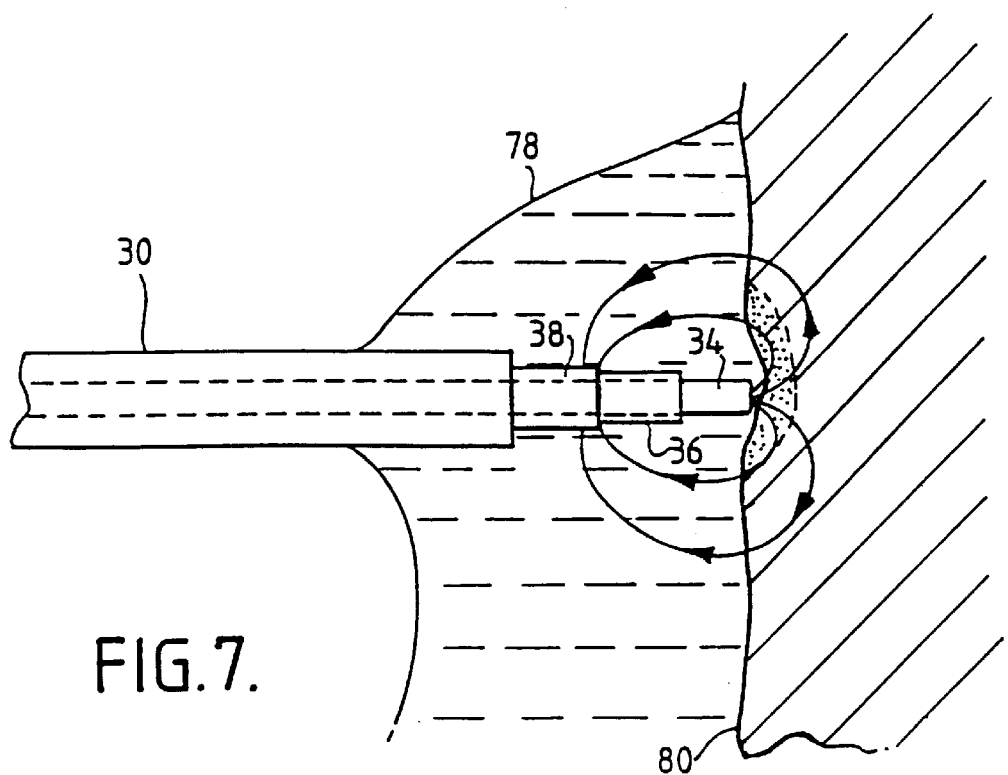
FIG. 7 is a diagrammatic side view of an instrument similar to that shown in FIG. 6, showing the use of the instrument for tissue desiccation or coagulation.

FIG. 7 illustrates the use of an electrode unit similar to that of FIG. 2 used for tissue desiccation. In the desiccation mode, output power is delivered to the electrodes in a first output range, so that current flows from the active electrode 34 to the return electrode 38. As described above, the output power causes the saline solution adjacent to the active electrode 34 to become heated, preferably to a point at or near the boiling point of the saline solution. This creates small vapour bubbles on the surface of the active electrode 14 that increase the impedance about the active electrode 34.

The vapour bubbles around the active electrode 34 coalesce into a vapour pocket 82 which completely envelopes the active electrode. This vapour is pure water, and has negligible conductivity. Consequently, any body tissue 80 intruding into the vapour pocket 82 represents a preferential conductive pathway for the arcs 84 within the vapour pocket. Accordingly, the preferred current path goes out of the active electrode 34 at the point of tissue contact, through the tissue 80, and then back to the return electrode 38 via the saline solution, as shown in FIG. 7.

The invention has particular application in desiccating tissue. For tissue desiccation, one preferred approach is to contact only part of the active electrode to the tissue, with the remainder of the active electrode remaining remote from the tissue and surrounded by saline solution so that current can pass from the active to return electrode, via the saline solution, without passing through the tissue. For example, in the embodiment shown in FIG. 7, only the distal portion of the active electrode contacts the tissue, with the proximal portion remaining spaced away from the tissue.

The invention can achieve desiccation with no or minimal charring of the tissue. When the active electrode 34 contacts the tissue 80, current passes through the tissue, causing the tissue at and around the contact point to desiccate. Alternatively, coagulation or desiccation can take place indirectly, with the active electrode 34 heating saline adjacent to, or absorbed in the tissue. The area and volume of desiccated tissue expands generally radially outward from the point of contact.

In the embodiment shown in FIG. 7, the exposed treatment portion of the active electrode 34 is longer than it is wide. This allows the electrode tip to contact the tissue surface while still maintaining most of the exposed treatment portion out of contact with the tissue even when the instrument is angled with respect to the tissue surface. Because most of the exposed portion of the electrode is out of contact with the tissue, the current path will more easily shift, upon desiccation of a sufficient tissue volume, from the path through the tissue to a path that goes directly from the active electrode to the saline solution.

In the electrode unit shown in FIG. 3 the exposed portion of the active electrode 34 is relatively short compared with the length of the insulation member 36 between the active electrode 34 and the return electrode 38. With such an electrode configuration, bistable operation of the instrument inherent in the hysteresis characteristic described above with reference to FIG. 4 applies, in that the instrument can be used in a desiccation mode or in a vaporisation mode of lower power. In some circumstances, particularly if the exposed treatment portion of the active electrode is long, bistable operation may be difficult to achieve.

Measures to overcome this difficulty will now be described with reference to FIG. 8 which shows an electrode unit comprising a shaft 30 constituted by a semi-flexible tube made of stainless steel or phynox electroplated in copper or gold, with an electrode assembly 32 at a distal end thereof. The electrode assembly 32 includes a central active electrode 34, made for example of tungsten, having an elongate exposed treatment portion 34A (which may be referred to as a "needle" electrode), and an integral central conductor 34B. A cylindrical ceramic insulation sleeve 36 surrounds the conductor 34B, and a return electrode 38, which is constituted by the distal end portion of the shaft 30, abuts a proximal end of the sleeve 36. An outer insulating polyimide coating 40 surrounds the proximal portion of the shaft adjacent the return electrode 38, thereby providing the return electrode with an annular fluid contact surface extending from the edge of the coating 40 to the insulation sleeve 36. The insulation sleeve 36 has a distal end face 36A of a diameter such that the step radius (i.e. the distance between the circumferential edge of the end face 36A and the outside diameter of the active electrode 34) is at least ¹⁄₂₀th of the length of the exposed active electrode treatment portion 34A. The insulation sleeve 36 thus has a shoulder (or step) which is coaxial with the active electrode 34. In use, this step prevents local arcing which could otherwise occur at the proximal end of the exposed active electrode treatment portion 34A, rendering the distal end of the treatment portion 34A ineffective.

To consider the operation of the electrode in more detail, when the electrode unit is operated in a tissue cutting or vaporising mode, a vapour bubble is formed around the active electrode treatment portion 34A. This bubble is sustained by arcing within it. The greater the applied voltage, the greater is the size of the bubble. The energy dissipated by each arc is impedance-limited by the remaining fluid in the conduction path and by the source impedance of the generator. However, an arc behaves as a negative impedance in that if the energy in the arc is sufficiently high, an ionised path of very low impedance is formed. This can lead to an unstable condition of ever-decreasing ionised path impedance unless the impedance of the fluid between the bubble and the return electrode is sufficient to act as a limit on dissipated power. It is also possible for the vapour pocket around the active electrode treatment portion to encroach the return electrode. In these circumstances, the arc energy is limited only by generator source impedance, but such power limitation is poor and cannot be adjusted according to electrode size. For these reasons, the dimensions and configuration of the insulation sleeve 36 should be such as to define a minimum conduction path length of 1 mm between the active electrode treatment portion 34A and the fluid contact surface of the return electrode 38. This minimum path length is, in the case of the embodiment shown in FIG. 8, the length a of the sleeve 36 plus the step radius c, as shown in FIG. 8.

A further consideration is the possibility of a vapour pocket forming only over part of the exposed treatment portion 34A of the active electrode 34. When the applied voltage and power are sufficiently high, a vapour pocket will form around the active electrode exposed treatment portion. Preferably, the pocket is formed uniformly over the entire length of the treatment portion. In such a situation, the load impedance presented to the generator can change by as much as a factor of 20. However, when there are significant differences in the conduction path length between the return electrode fluid contact surface and different parts of the exposed active electrode treatment portion 34A, a voltage gradient is established over the length of each electrode. Preferably, the fluid contact surface is large enough and has an aspect ratio such that its length is at least as great as its diameter so as to minimise a voltage gradient over its surface. Nevertheless, with some insulation sleeve and active electrode configurations, the voltage gradient can be sufficiently large to enable vapour pocket formation only over that part of the exposed treatment portion closest to the fluid contact surface, leaving the extreme distal end of the exposed treatment portion still in contact with the conductive fluid. Thus, the voltage gradient is established within the conductive fluid where the edge of the vapour pocket intersects the surface of the active electrode treatment portion 34A. The electrical behaviour of such a partially enveloped active electrode treatment portion is very different from that of a fully enveloped treatment portion. The impedance transition from the wetted state to the vapour enveloped state is far less marked than described above with reference to FIG. 4. In terms of controlling generator output by sensing peak voltage, the behaviour of the electrode assembly is no longer bistable. However, the power demand is considerably higher as a result of the vaporisation voltage presented across the low impedance wetted region of the active electrode treatment portion. The clinical effect is not only the required vaporisation, but also a potentially undesirable thermal damaging effect resulting from the increased power dissipation. This effect may, however, be beneficial in these types of electrodes which are typically used for cutting, wherein it is desirable to seal blood vessels simultaneously with the cutting action.

Thus, system behaviour involves bistability between the wetted (or desiccate) and the vaporise states. The hysteresis between these states is highly interactive with electrode construction, tissue and engagement angle. The phenomenon is largely due to an impedance transition between states. The impedance transition is determined by the power required to convert wetting saline to vapour. If saline is excluded from the circuit, the impedance transition occurs at a lower power, and a consequently higher impedance.

Figure 11:
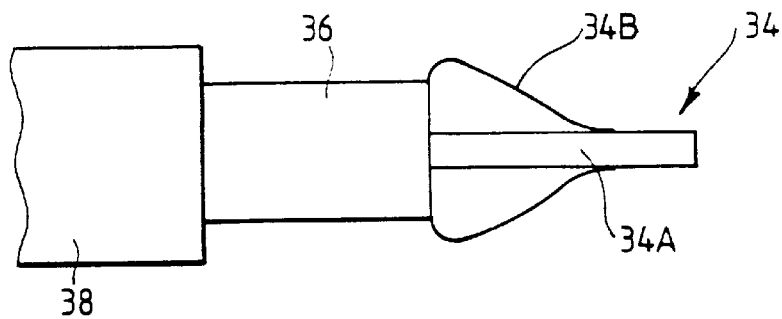
FIG. 11 is a diagrammatic side view similar to that of FIG. 8, but showing a partially-enveloped active electrode.

The key design features are the ratios which describe the proximity variance of the active electrode treatment portion 34A with respect to the return electrode 38. To best describe the performance effects of these ratios, it is easiest to consider extremes. For example, if the ratio were very high, which would infer an elongate active electrode 34, the highest current density occurs at the shortest electrical path. RF current travelling through the saline creates a voltage gradient within the saline. This gradient manifests itself as a gradient along the length of the active electrode 34. The electrical gradient falls until the tip, which is furthest away from the return electrode 38 is at the same potential as the surrounding saline. FIG. 11 illustrates the state of such an active electrode 34.

This figure illustrates a partially-enveloped active electrode 34. The significance of this is that the states of vaporise and desiccate are no longer unique. The high impedance transition from the wetted (desiccate state) to the vapour (vaporise state) only occurs as a gradual vapour-enveloped section 34B, which leads to very high currents at the wetted section. The consequence of exceeding the maximum ratio, is, therefore, to prevent bistable operation of the electrode and power efficient operation.

Figure 8:
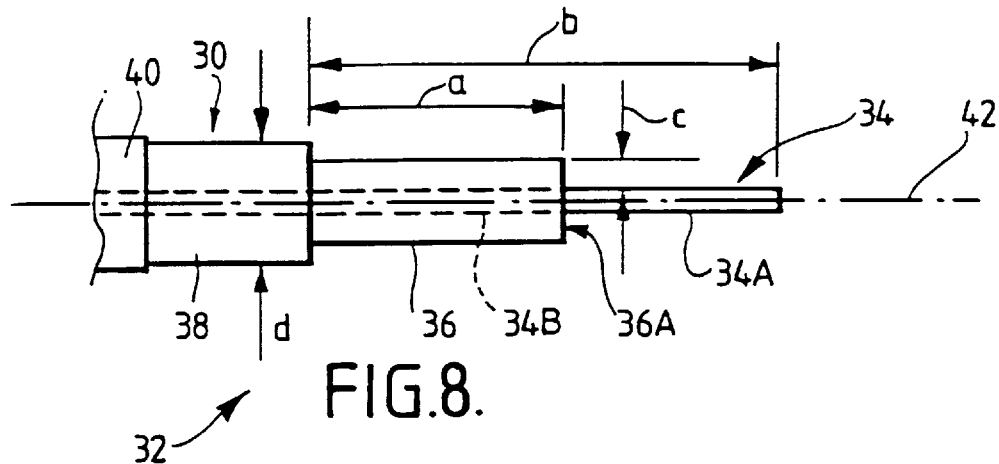
FIGS. 8, 9 and 10 are side views of further electrosurgical instruments in accordance with the invention, showing different active electrode, return electrode and insulator configurations.

Partial enveloping of the active electrode treatment portion 34A can be largely avoided by ensuring that the ratio of the length of the conductive path between the furthermost point of the active electrode treatment portion and the length of the shortest conductive path between the active electrode treatment portion and the fluid contact surface is less than or equal to 2:1, i.e. $b/(a+c) \leq 2$ (see FIG. 8).

Figure 12:
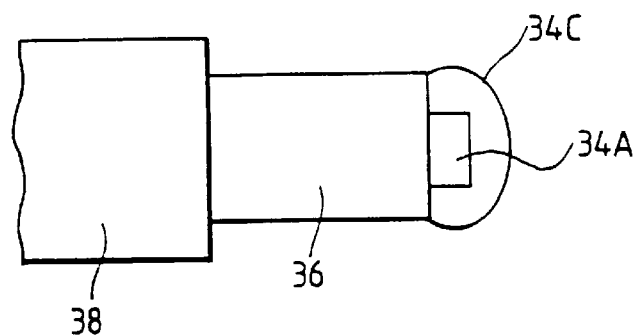
FIG. 12 is a diagrammatic side view similar to that of FIG. 11, but showing a short, completely-enveloped active electrode.

In the other extreme, ratios less than 1.25 will increase the bistable behaviour of the electrode. FIG. 12 illustrates the state of such an electrode assembly, where there is no gradual enveloping of the active electrode treatment portion 34A, this entire portion being completely enveloped in vapour, as indicated by the reference 34C. This electrode will instantaneously flip between states, with consequent large changes in power. This is due to the entire circumference of the active electrode 34 being at a similar potential. All saline around the active electrode 34 is, therefore, at the same potential, and absorbs the same power levels. The transition threshold from the wetted state to the vaporise state, is, therefore, very well defined. When this transition state is reached or exceeded, the active electrode 34 will flip into the vaporise state, and absorb far less power. Whilst this might be desirable, it is then very difficult to control the active electrode 34 with maximum power in the wetted state. This is, of course, desirable for maximum desiccation. It is highly undesirable to remove tissue when desiccation is demanded by the user, i.e. for the active electrode 34 to inadvertently flip to the vaporise state. Thus, lower ratios are avoided, as they enhance bistability at the cost of not being able to guarantee a given state. The impedance power characteristic in the vapour state is also very steep, which leads to difficulty in control, as small power increments may either cause electrode destruction, or for the electrode to fall out of the vapour state back into the wetted state.

Control of the vaporise/desiccate states can be ensured by arranging for the ratio of the length of the shortest conductive path through the saline between the furthermost point of the active electrode treatment portion 34A and the fluid contact surface of the return electrode 38, to the length of the shortest conductive path through the saline between the exposed fluid contact surface and the exposed active electrode treatment portion to be greater than or equal to 1.25:1, i.e. $b/(a+c) \geq 1.25$ (see FIG. 8).

Figure 13:
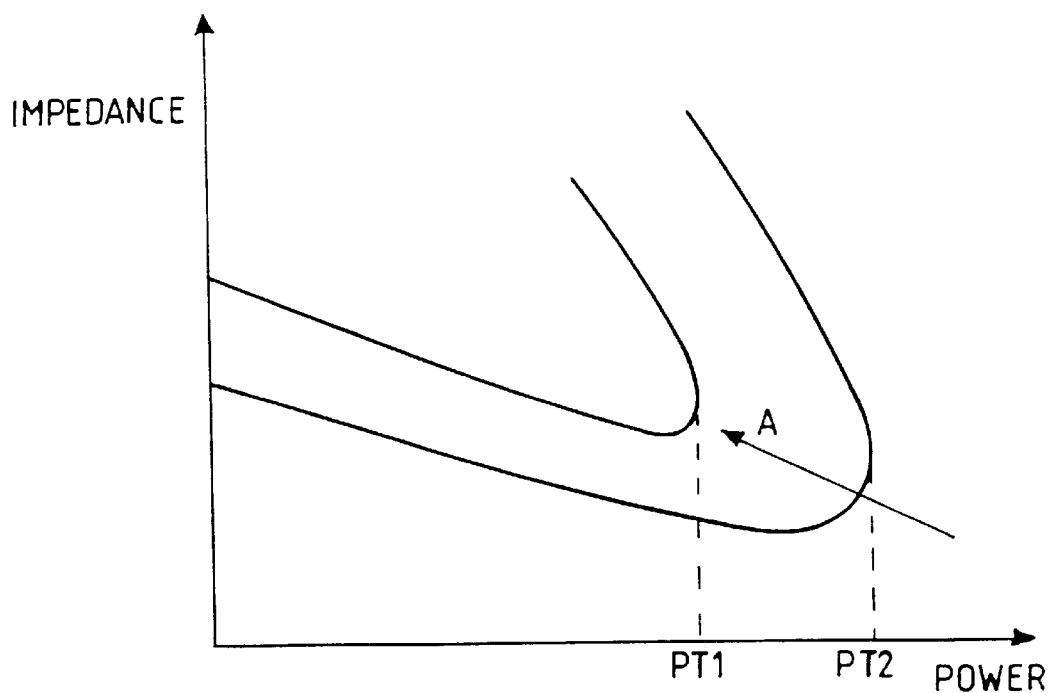
FIG. 13 is a power/impedance characteristic showing variations as the electrosurgical instrument of the invention approaches tissue.

When the active electrode 34 is brought into close proximity to tissue, the transition threshold between the desiccate and vaporise states changes. As all tissue will be of higher impedance than the surrounding saline, the transition power threshold will reduce. Thus, control of the delivered RF power and voltage are dynamic to compensate for this effect. This permits maximum power delivery without exceeding the power threshold, thereby ensuring maximum desiccation power for the prevailing circumstances. FIG. 13 illustrates the theoretical effects on the active electrode 34 as it approaches tissue, as indicated by the arrow A. The two curves represent the relationship between the load impedance presented to the electrode assembly as a function of delivered electrosurgical power, at two different separations between the active electrode tip and the adjacent tissue surface. As described in the specification of our International patent application WO97/24993, the transition (vaporisation) threshold is dependent upon convection around the active electrode. Obviously, close proximity of the active electrode with tissue will interfere with these convection currents, thereby reducing the transition threshold, as shown by the reduction in power threshold from $P_{T1}$ to $P_{T2}$, as the tip of the active electrode approaches tissue. The other effect of tissue proximity, is to change the electrical gradient across the surface of the active electrode. Depending on the relative approach made by the active electrode to tissue, the bistable state may either be enhanced or degraded. For example, a long thin active electrode, which may not have a truly bistable state (for the reasons outlined above), may attain bistable behaviour. This is likely to occur by an end-on approach to the tissue. Consequently, the maximum ratio of 2:1 referred to above can be extended slightly when the distal portion of the active electrode is in contact with, or partially buried in, tissue. Such an active electrode would typically be used for simultaneous cutting of tissue and sealing of adjacent blood vessels.

Moreover, electrode assemblies with a design ratio greater than 2:1 in the treatment axis can be used for haemostatic effects when vaporising, or purely for a haemostatic electrosurgical instrument, as assemblies with such a ratio will not exhibit bistable effects between the wetted and vaporise states.

In some circumstances, it may be found that the conductive path length between the active and return electrodes is too long to allow vaporisation of the conductive fluid due to the consequent large series impedance represented by the fluid. Too large a voltage drop may result in a preset voltage threshold being reached before vaporisation can be achieved. Preferably, then, the ratio of the greatest conduction path length to the annular peripheral length of the return electrode fluid contact surface is no more than 1.43:1. In the case of a cylindrical fluid contact surface which is coaxial with the active electrode, the ratio of the greatest conduction path length to the fluid contact surface diameter is less than or equal to 4.5:1. Thus, with reference to FIG. 8, b/d≦4.5.

The primary use of the electrode unit shown in FIG. 8 is for cutting tissue, with at least part of the active electrode treatment portion 34A buried in the tissue to be treated and with the generator operated in the vaporisation portion of the impedance/power characteristics shown in FIG. 4.

Figure 9:
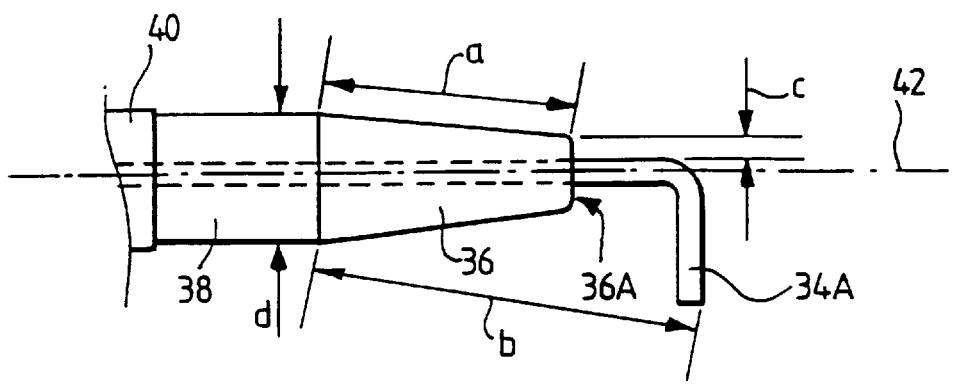

Alternative active electrode configurations include forming the exposed treatment portion 34A as a hook, as shown in FIG. 9. In this case, the insulation sleeve is conical, tapering from the fluid contact surface of the return electrode 38 to the distal end face 36A.

Figure 10:
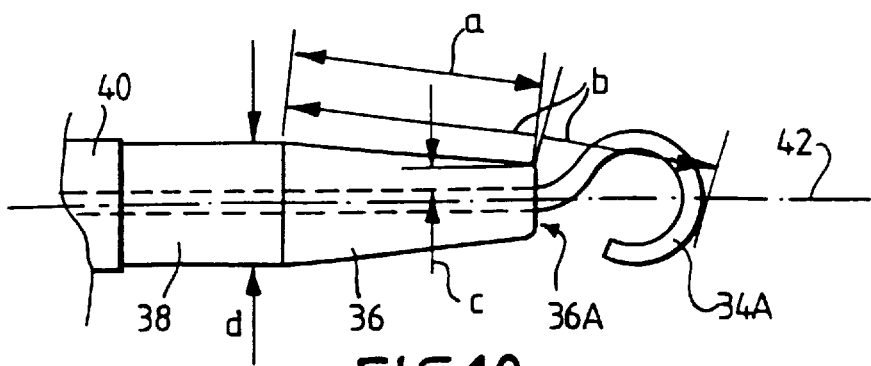

A further alternative, shown in FIG. 10 has an active electrode treatment portion 34A in the shape of a looped hook.

In the embodiments of FIGS. 8, 9 and 10, it will be seen that the dimensions a, b, c, d are such as to fall within the ratio limits described above. Furthermore, in each case, the electrode assembly may be viewed as having a treatment axis 42, being the axis along which the instrument may be introduced towards the tissue, the return electrode 38 being set back in the direction of the treatment axis from the active electrode exposed treatment portion 34A For the purpose of comparing the different conduction path lengths between the return electrode and different parts of the active electrode treatment portion, paths in a common plane should be considered, the plane containing the treatment axis 42. In the case of the views of FIGS. 8, 9 and 10, the illustrated path lengths are, of course, in the plane of the paper bearing the views.

We claim:

1. An electrosurgical instrument for the treatment of tissue in the presence of an electrically conductive fluid medium, the instrument comprising an instrument shaft and an electrode assembly at a distal end of the shaft, wherein the electrode assembly comprises:

a single active electrode having an exposed tissue treatment portion, a return electrode having an exposed fluid contact surface, and an insulating member positioned between and electrically insulating the active electrode and the return electrode and serving to space apart the exposed treatment portion of the active electrode, and the exposed fluid contact surface of the return electrode, the fluid contact surface of the return electrode being set back in the direction of a treatment axis of the assembly from the active electrode exposed treatment portion, and wherein the dimensions and configuration of the exposed treatment portion, the exposed fluid contact surface and the insulation member are such that when the electrode assembly is immersed in a conductive fluid medium the ratio of (i) the length of the shortest conduction path ($P_1$) through the fluid medium between the exposed fluid contact surface and that part of the exposed treatment portion which is furthest from the exposed fluid contact surface, to (ii) the length of the shortest conduction path ($P_2$) through the fluid medium between the exposed fluid contact surface and the exposed treatment portion, is greater than or equal to 1:25 to 1.

2. An instrument according to claim 1, wherein the exposed treatment portion of the active electrode projects in a first direction from the insulation member, and the insulating member surrounds the active electrode and, between the active electrode exposed portion and the return electrode fluid contact surface, projects outwardly in a second direction perpendicular to the first direction to define an insulation barrier to divert electrical current flow through the fluid medium thereby to increase said shortest conduction path length ($P_2$) between the exposed fluid contact surface and the exposed treatment portion.

3. An instrument according to claim 1, wherein the first direction defines a treatment axis and said two shortest conduction paths ($P_1$, $P_2$) lie in a common plane containing the treatment axis.

4. An instrument according to claim 1, wherein the length of said shortest conduction path ($P_2$) through the fluid medium between the exposed fluid contact surface and the exposed treatment portion is at least 1 mm.

5. An instrument according to claim 1 wherein the exposed fluid contact surface is generally cylindrical and has a length and a diameter, the length of the fluid contact surface being at least as great as its diameter and wherein the ratio of (i) the shortest conduction path ($P_1$) through the fluid medium between the fluid contact surface and that part of the exposed treatment portion which is furthest from the fluid contact surface, to (ii) the fluid contact surface diameter, is at most 4.5 to 1.

6. An instrument according to claim 1, wherein the ratio of (i) the length of the shortest conduction path ($P_1$) through the fluid medium between the exposed fluid contact surface and that part of the exposed treatment portion which is furthest from the exposed fluid contact surface, to (ii) the length of the shortest conduction path ($P_2$) through the fluid medium between the exposed fluid contact surface and the exposed treatment portion, is greater than or equal to 2 to 1.

7. An instrument according to claim 1, wherein the return electrode comprises a conductive sleeve located around the insulation member behind the treatment portion of the active electrode.

8. An instrument according to claim 1, wherein the longitudinal spacing of the active electrode exposed treatment portion and the return electrode exposed fluid contact surface is at least 1 mm.

9. An instrument according to claim 8, wherein the return electrode has a fluid contact surface encircling the insulation member, and wherein the ratio of (i) the longitudinal distance between the distal end of the active electrode exposed treatment portion and the distal edge of the exposed fluid contact surface of the return electrode to (ii) the circumference of the exposed fluid contact surface in the region of its distal edge is less than or equal to 1:43:1.

10. An instrument according to claim 1, wherein the instrument shaft comprises a metallic tube as its main structural element, and the return electrode is an integrally formed distal end portion of the tube.

11. An electrosurgical system comprising an instrument according to claim 1 and further comprising an electrosurgical generator for supplying radio frequency power to the instrument, the generator including an output stage having at least a pair of electrosurgical output connections connectible respectively to the active electrode and the return electrode of the instrument, a sensing circuit for deriving a sensing signal representative of the peak radio frequency output voltage developed between the output connections, and a power adjustment circuit for automatically causing a reduction in delivered output power when the sensing signal is indicative of a predetermined peak radio frequency output voltage having been reached.

12. A system according to claim 11, wherein the power adjustment circuit is operable to cause at least a 50% reduction in delivered output power when the sensing signal is indicative of said threshold having been reached, said reduction being effected with a period of 100 µs or less.

13. A system according to claim 11, wherein the power adjustment circuit is operable to effect said reduction in a period of 20 µs or less.

14. A system according to claim 11, wherein the output stage includes at least one radio frequency power device, and wherein the control circuitry is arranged such that the at least 50% reduction in output power is effected by reducing the period of conduction of the device during individual cycles of radio frequency oscillation independently of the supply voltage to the device.

15. A system according to claim 14, wherein the sensing circuit and the power adjustment circuits are operable repeatedly to effect a rapid reduction in the cycle by-cycle conduction period of the power device from a peak level to a trough level followed by a less rapid progressive increase in the conduction period until the conduction period again reaches its peak level, the rapid reduction and progressive increase sequence being repeated while simultaneously reducing the supply voltage to said output stage until said peak conduction period level can be reached without the output voltage exceeding said predetermined threshold.

16. A system according to claim 11, wherein the generator has a first output voltage range suitable for a tissue desiccation mode, and a second output voltage range suitable for a tissue vaporisation mode, the first output voltage range being such that the power supplied to the electrode assembly maintains the conductive fluid adjacent to the tissue treatment electrode substantially at boiling point for tissue coagulation or desiccation without creating a layer of vapour around the tissue treatment electrode, and the second output voltage range is such that the output power supplied to the electrode assembly for vaporisation of tissue is such as to maintain a vapour pocket surrounding the tissue treatment electrode.

17. A system according to claim 16, further comprising separate controls for actuating the generator to operate in its first and second output voltage ranges.

18. A system according to claim 17, wherein separate footswitches operatively connected to the generator constitute said separate controls.

19. A method of treating tissue using a bipolar electrode assembly, the assembly including an active electrode and a return electrode, the active electrode having an exposed treatment portion, and the return electrode having an exposed fluid contact surface spaced and set back from the exposed treatment portion, the method comprising the steps of:

(a) introducing the electrode assembly into a selected operation site;

(b) surrounding the electrode assembly with a conductive fluid so that the conductive fluid defines an electrical path between the active and return electrodes, (c) applying sufficient radio frequency output power to the electrode assembly to increase the temperature of the conductive fluid adjacent to the active electrode treatment portion without creating a layer of vapour around the treatment portion; and (d) locally applying heat by means of the treatment portion to treat tissue while maintaining the return electrode fluid contact surface out of contact with the tissue.

20. A method according to claim 19, wherein step (c) is such that the temperature of the conductive fluid adjacent to the active electrode treatment portion lies within the range of from 70° C. to 100° C., whereby the tissue to be treated is coagulated.

21. A method according to claim 19, wherein step (c) is such that the temperature of the conductive fluid adjacent to the active electrode treatment portion is at least 100° C., whereby the tissue to be treated is desiccated.

22. A method according to claim 19, wherein step (d) is such that heat is applied to the tissue by heating the conductive fluid adjacent thereto or absorbed thereby.

23. A method of vaporising tissue using a bipolar electrode assembly, the bipolar electrode assembly including an active electrode and a return electrode, the active electrode having an exposed treatment portion, and the return electrode having an exposed fluid contact surface, and an insulating member positioned between and electrically insulating the active electrode and the return electrode and serving to space apart the exposed treatment portion of the active electrode and the exposed fluid surface of the return electrode, the fluid contact surface of the return electrode being set back in the direction of a treatment axis of the assembly from the active electrode exposed treatment portion, the dimensions and configuration of the exposed treatment portion, the exposed fluid contact surface and the insulation member being such that, when the electrode assembly is immersed in a conductive fluid medium, the ratio of (i) the length of the shortest conduction path (P1) through the fluid medium, between the exposed fluid contact surface and that part of the exposed treatment portion which is furthest from the exposed fluid contact surface, to (ii) the length of the shortest conduction path (P2) through the fluid medium between the exposed fluid contact surface and the exposed treatment portion, is greater than or equal to 2:1, the method comprising the steps of:

(a) introducing the electrode assembly into a selected operation site;

(b) surrounding the electrode assembly with a conductive fluid;

(c) applying sufficient radio frequency output power to the electrode assembly to vaporise the conductive fluid adjacent to the active electrode treatment portion to create a vapour pocket surrounding the treatment portion; and (d) positioning the treatment portion of the active electrode adjacent to the tissue with the vapour pocket in contact with the tissue while maintaining the return electrode out of contact with the tissue.

24. A method of vaporising and haemostatically treating tissue using a bipolar electrode assembly, the bipolar electrode assembly including an active electrode and a return electrode, the active electrode having an exposed treatment portion, the method comprising the steps of:

(a) introducing the electrode assembly into a selected operation site;

(b) surrounding the electrode assembly with a conductive fluid;

(c) alternating the application of sufficient radio frequency output power to the electrode assembly to (i) vaporise the conductive fluid adjacent to the active electrode treatment portion to create a vapour pocket surrounding the treatment portion, and (ii) to increase the temperature of the conductive fluid adjacent to the active electrode treatment portion without creating a layer of vapour around the treatment-portion; and (d) positioning the treatment portion of the active electrode adjacent to the tissue while maintaining the return electrode out of contact with the tissue.

25. A method of haemostatically treating tissue using a bipolar electrode assembly, the bipolar electrode assembly including an active electrode and a return electrode, the active electrode having an exposed treatment portion, the method comprising the steps of:
(a) introducing the electrode assembly into a selected operation site;
(b) surrounding the electrode assembly with a conductive fluid;
(c) applying maximum radio frequency output power to the electrode assembly to heat the conductive fluid adjacent to the active electrode treatment portion without creating a layer of vapour around the treatment portion; and
(d) positioning the treatment portion of the active electrode adjacent to the tissue with the heated conductive fluid in contact with the tissue while maintaining the return electrode out of contact with the tissue.

26. A method of treating tissue using a bipolar electrode assembly, the assembly including a single active electrode having an exposed treatment portion, a return electrode having an exposed fluid contact surface, and an insulating member positioned between and electrically insulating the active electrode and the return electrode and serving to space apart the exposed treatment portion of the active electrode and the exposed fluid surface of the return electrode, the fluid contact surface of the return electrode being set back in the direction of a treatment axis of the assembly from the active electrode exposed treatment portion, the dimensions and configuration of the exposed treatment portion, the exposed fluid contact surface and the insulation member being such that, when the electrode assembly is immersed in a conductive fluid medium, the ratio of (i) the length of the shortest conduction path (P1) through the fluid medium between the exposed fluid contact surface and that part of the exposed treatment portion which is furthest from the exposed fluid contact surface, to (ii) the length of the shortest conduction path (P2) through the fluid medium between the exposed fluid contact surface and the exposed treatment portion, is greater than or equal to 2:1, the method comprising the steps of:
(a) introducing the electrode assembly into a selected operation site;
(b) surrounding the electrode assembly with a conductive fluid so that the conductive fluid defines an electrical path between the active and return electrodes;
(c) applying sufficient radio frequency output power to the electrode assembly to increase the temperature of the conductive fluid adjacent to the active electrode treatment portion without creating a layer of vapour around the treatment portion; and
(d) locally applying heat by means of the treatment portion to treat tissue while maintaining the return electrode fluid contact surface out of contact with the tissue.

27. A method of vaporising tissue using a bipolar electrode assembly, the bipolar electrode assembly including a single active electrode having an exposed treatment portion, and the return electrode having an exposed fluid contact surface, and an insulating member positioned between and electrically insulating the active electrode and the return electrode and serving to space apart the exposed treatment portion of the active electrode and the exposed fluid surface of the return electrode, the fluid contact surface of the return electrode being set back in the direction of a treatment axis of the assembly from the active electrode exposed treatment portion, the dimensions and configuration of the exposed treatment portion, the exposed fluid contact surface and the insulation member being such that, when the electrode assembly is immersed in a conductive fluid medium, the ratio of (i) the length of the shortest conduction path (P1) through the fluid medium between the exposed fluid contact surface and that part of the exposed treatment portion which is furthest from the exposed fluid contact surface, to (ii) the length of the shortest conduction path (P2) through the fluid medium between the exposed fluid contact surface and the exposed treatment portion, is greater than or equal to 2:1, the method comprising the steps of:
(a) introducing the electrode assembly into a selected operation site;
(b) surrounding the electrode assembly with a conductive fluid;
(c) applying sufficient radio frequency output power to the electrode assembly to vaporise the conductive fluid adjacent to the active electrode treatment portion to create a vapour pocket surrounding the treatment portion;
(d) positioning the treatment portion of the active electrode adjacent to the tissue with the vapour pocket in contact with the tissue while maintaining the return electrode out of contact with the tissue.

28. A method of vaporising and haemostatically treating tissue using a bipolar electrode assembly, the bipolar electrode assembly including a single active electrode having an exposed treatment portion, a return electrode having an exposed fluid contact surface, and an insulating member positioned between and electrically insulating the active electrode and the return electrode and serving to space apart the exposed treatment portion of the active electrode and the exposed fluid surface of the return electrode, the fluid contact surface of the return electrode being set back in the direction of a treatment axis of the assembly from the active electrode exposed treatment portion, the dimensions and configuration of the exposed treatment portion, the exposed fluid contact surface and the insulation member being such that, when the electrode assembly is immersed in a conductive fluid medium, the ratio of (i) the length of the shortest conduction path (P1) through the fluid medium between the exposed fluid contact surface and that part of the exposed treatment portion which is furthest from the exposed fluid contact surface, to (ii) the length of the shortest conduction path (P2) through the fluid medium between the exposed fluid contact surface and the exposed treatment portion, is greater than or equal to 2:1, the method comprising the steps of:
(a) introducing the electrode assembly into a selected operation site;
(b) surrounding the electrode assembly with a conductive fluid;
(c) alternating the application of sufficient radio frequency output power to the electrode assembly to (i) vaporise the conductive fluid adjacent to the active electrode treatment portion to create a vapour pocket surrounding the treatment portion, and (ii) increase the temperature of the conductive fluid adjacent to the active electrode treatment portion without creating a layer of vapour around the treatment portion; and
(d) positioning the treatment portion of the active electrode adjacent to the tissue while maintaining the return electrode out of contact with the tissue.

29. A method of haemostatically treating tissue using a bipolar electrode assembly, the bipolar electrode assembly including a single active electrode having an exposed tissue treatment portion, a return electrode having an exposed fluid contact surface, and an insulating member positioned between and electrically insulating the active electrode and the return electrode and serving to space apart the exposed treatment portion of the active electrode and the exposed fluid surface of the return electrode, the fluid contact surface of the return electrode being set back in the direction of a treatment axis of the assembly from the active electrode exposed treatment portion, the dimensions and configuration of the exposed treatment portion, the exposed fluid contact surface and the insulation member being such that, when the electrode assembly is immersed in a conductive fluid medium, the ratio of (i) the length of the shortest conduction path (P1) through the fluid medium, between the exposed fluid contact surface and that part of the exposed treatment portion which is furthest from the exposed fluid contact surface, to (ii) the length of the shortest conduction path (P2) through the fluid medium between the exposed fluid contact surface and the exposed treatment portion, is greater than or equal to 2:1, the method comprising the steps of:

(a) introducing the electrode assembly into a selected operation site;

(b) surrounding the electrode assembly with a conductive fluid;

(c) applying maximum radio frequency output power to the electrode assembly to heat the conductive fluid adjacent to the active electrode treatment portion without creating a layer of vapour around the treatment portion; and (d) positioning the treatment portion of the active electrode adjacent to the tissue with the heated conductive fluid in contact with the tissue while maintaining the return electrode out of contact with the tissue.

30. A method of vaporising and haemostatically treating tissue using a bipolar electrode assembly, the bipolar electrode assembly including a single active electrode having an exposed tissue treatment portion, a return electrode having an exposed fluid contact surface, and an insulating member positioned between and electrically insulating the active electrode and the return electrode and serving to space apart the exposed treatment portion of the active electrode and the exposed fluid surface of the return electrode, the fluid contact surface of the return electrode being set back in the direction of a treatment axis of the assembly from the active electrode exposed treatment portion, the dimensions and configuration of the exposed treatment portion, the exposed fluid contact surface and the insulation member being such that, when the electrode assembly is immersed in a conductive fluid medium, the ratio of (i) the length of the shortest conduction path ($P_1$) through the fluid medium between the exposed fluid contact surface and that part of the exposed treatment portion which is furthest from the exposed fluid contact surface, to (ii) the length of the shortest conduction path ($P_2$) through the fluid medium between the exposed fluid contact surface and the exposed treatment portion, is greater than or equal to 2:1, the method comprising the steps of:

(a) introducing the electrode assembly into a selected operation site;

(b) surrounding the electrode assembly with a conductive fluid;

(c) applying sufficient radio frequency output power to the electrode assembly to vaporise the conductive fluid adjacent to the active electrode treatment portion to create a vapour pocket surrounding the treatment portion; and (d) at least partially burying the treatment portion of the active electrode in the tissue while maintaining the return electrode out of contact with the tissue.

31. An electrosurgical system for the treatment of tissue, including:

an electrosurgical generator which produces a radio frequency oscillating electrical output across a pair of output connections;

an electrosurgical instrument having an active, tissue treatment electrode connected to one of the generator output connections, and a return electrode connected to another of the generator output connections, the return electrode being electrically insulated from the active electrode, and providing a path for the oscillating output from the generator to flow to and from the active electrode when a conduction path between the electrodes is completed by an electrically conducting fluid, wherein, when the electrodes are immersed in an electrically conducting fluid, the ratio of (a) the length of the shortest conduction path through the fluid between the return electrode and a part of the active electrode most distal from the return electrode, to (b) the length of the shortest conduction path through the fluid between the return electrode and a part of the active electrode most proximal to the return electrode is greater than 1.25:1;

the generator controlling the power of the radio frequency oscillating output so that, in use, power can be dissipated into the electrically conducting fluid by current passing between the electrodes through the electrically conducting fluid, without creating a vapour pocket around at least a part of the active electrode.

32. An electrosurgical system according to claim 31 wherein, when the electrodes are immersed in an electrically conducting fluid, the ratio of (a) the length of the shortest conduction path through the fluid between the return electrode and a part of the active electrode most distal from the return electrode, to (b) the length of the shortest conduction path through the fluid between the return electrode and a part of the active electrode most proximal to the return electrode is greater than 2:1.

33. An electrosurgical system according to claim 31 wherein the generator is additionally selectively operable to adjust the output power of the radio frequency output signal to cause the creation of a vapour pocket around at least a part of the active electrode, and wherein, when the electrodes are immersed in an electrically conducting fluid, the ratio of (a) the length of the shortest conduction path through the fluid between the return electrode and a part of the active electrode most distal from the return electrode, to (b) the length of the shortest conduction path through the fluid between the return electrode and a part of the active electrode most proximal to the return electrode is greater than 2:1.

* * * * *